United States Patent [19]

Huang et al.

[11] Patent Number: 5,059,610

[45] Date of Patent: * Oct. 22, 1991

[54] QUINOLINE DERIVATIVES AND THEIR USE AS ANTAGONISTS OF LEUKOTRIENE $D_4$

[75] Inventors: Fu-Chi Huang, Gwynedd; Robert A. Galemmo, Jr., Ambler; Henry F. Campbell, North Wales, all of Pa.

[73] Assignee: Rhone-Poulenc Rorer Pharmaceuticals Inc., Fort Washington, Pa.

[ * ] Notice: The portion of the term of this patent subsequent to Apr. 24, 2007 has been disclaimed.

[21] Appl. No.: 477,896

[22] PCT Filed: Nov. 1, 1988

[86] PCT No.: PCT/US88/C3897

§ 371 Date: Apr. 20, 1990

§ 102(e) Date: Apr. 20, 1990

[87] PCT Pub. No.: WO89/04305

PCT Pub. Date: May 18, 1989

[51] Int. Cl.$^5$ .................. C07D 401/10; C07D 215/12; A61K 31/41; A61K 31/47
[52] U.S. Cl. .................................... 514/314; 514/311; 546/472; 546/174; 546/176
[58] Field of Search .................. 546/174, 172, 176; 514/311, 314

[56] References Cited

U.S. PATENT DOCUMENTS

| | | | |
|---|---|---|---|
| 4,920,130 | 4/1990 | Huang et al. | 546/174 |
| 4,920,131 | 4/1990 | Huang et al. | 546/174 |
| 4,920,132 | 4/1990 | Huang et al. | 546/174 |
| 4,920,133 | 4/1990 | Huang et al. | 546/174 |

FOREIGN PATENT DOCUMENTS

89/05294 6/1989 PCT Int'l Appl. .................. 546/174

Primary Examiner—David B. Springer
Attorney, Agent, or Firm—Martin F. Savitzky; James A. Nicholson; Alexis Barron

[57] ABSTRACT

This invention relates to quinolinyl-diaryl compounds and their use as leukotriene $D_4$ antagonists for the treatment of hypersensitive disorders.

43 Claims, No Drawings

QUINOLINE DERIVATIVES AND THEIR USE AS ANTAGONISTS OF LEUKOTRIENE D₄

CROSS-REFERENCE TO RELATED APPLICATION

This is a continuation-in-part of application Ser. No. 07/116,420, filed Nov. 3, 1987, now U.S. Pat. No. 4,920,132.

FIELD OF INVENTION

This invention relates to quinolinyl phenyl compounds and their use as valuable pharmaceutical agents, particularly as lipoxygenase inhibitors and/or leukotriene antagonists possessing anti-inflammatory and anti-allergic properties.

SUMMARY OF THE INVENTION

This invention relates to the compounds described by the general Formula I and to therapeutic compositions comprising as active ingredient a compound of Formula I:

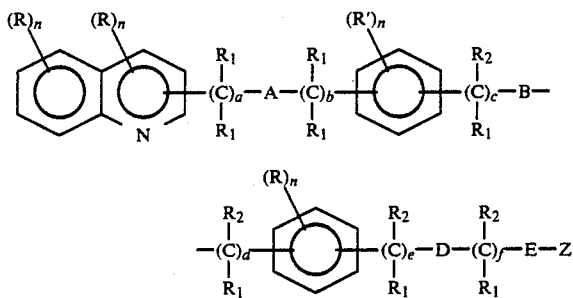

where:
A is O or S;
B is O, S, SO, SO₂ NR₁,

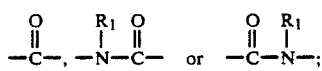

D is O, S, NR₁,

or a chemical bond;
E is a chemical bond or

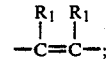

a is 0–2;
b is 0–1;
c is 0–4;
d is 0–5;
e is 0–4;
f is 0–5;
n is 0–2;
R is independently hydrogen, alkyl, hydroxy, alkoxy, carboxy, carbalkoxy, halo, nitro, haloalkyl, cyano or acyl;
R' is independently hydrogen, alkyl, hydroxy, alkoxy, halo or haloalkyl;
R₁ is independently hydrogen, alkyl or aralkyl;
R₂ is —(CH₂)$_x$—X, where x is 0–3;
X is hydrogen, alkyl, alkenyl, cycloalkyl, aryl aralkyl, hydroxy, alkoxy, aralkoxy, amino, mono-and dialkylamino, aralkylamino, acylamino, carbamyl, carboxy, carbalkoxy, tetrazolyl, or acylsulfonamido;
vicinal R₂ groups together may be (CH₂)$_y$—where y is 1–4, thus forming a 3–6 membered ring;
geminal R₁ and R₂ groups may together form a spiro substituent, —(CH₂)$_z$—, where z is 2 to 5;
geminal R₁ or R₁ and R₂ groups may together form an alkylidenyl substituent, =CHR₁;
Z is —COOR₁, CH, $$-\overset{O}{\underset{\|}{C}}NHSO_2R_3, \quad -\overset{O}{\underset{\|}{C}}N(R_1)_2,$$

—OR₁, tetrazolyl or substituted tetrazolyl where the substituent may be alkyl, carboxyalkyl or carbalkoxyalkyl;
R₃ is hydrogen, alkyl, haloalkyl, phenyl or benzyl; and pharmaceutically acceptable salts thereof.

The compounds of Formula I contain at least three aromatic rings, which may be designated as shown in Formula II below, and for which their substitution pattern along the chain with respect to each other is shown also below.

Formula II

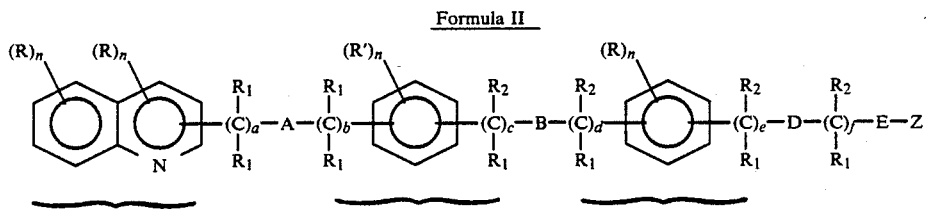

Ring I        Ring II        Ring III

The substitution pattern of the quinoline ring, that is Ring I, is preferably at the 2- position for extending the side chain. As this side chain progresses from the quinoline ring, the two phenyl rings, designated Ring II and Ring III may be substituted along the chain in the ortho, meta or para positions with respect to each other and Ring II may also be substituted in the ortho, meta and para positions in respect to the quinoline ring.

The preferred substitution pattern for ring II is meta or para, that is:

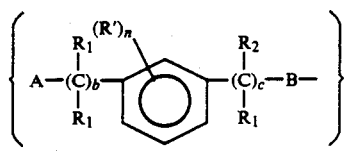

or

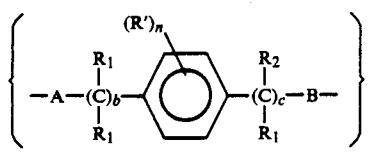

Ring III may be substituted equally in the ortho, meta or para positions, that is:

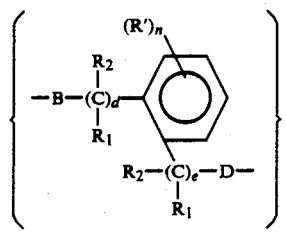

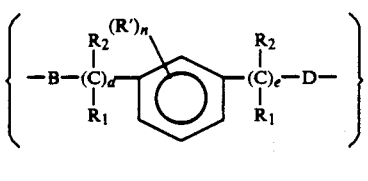

or

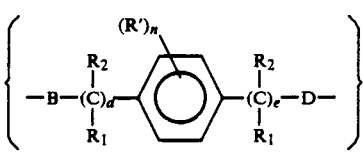

Further preferred compounds of this invention are described by Formula V below:

Formula V

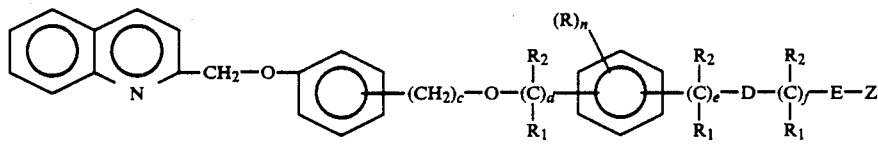

where $c+d=1-3$ and R, $R_1$, $R_2$, e, f, n, D, E and Z are as described above.

The preferred compounds of Formula V are those where Z is $-COOR_1$; $-CN$;

$$-\overset{O}{\underset{\|}{C}}NHSO_2R_3$$

or tetrazolyl.

In addition, the present invention relates to the method of using these compounds as lipoxygenase inhibitors and/or leukotriene antagonists possessing anti-inflammatory and anti-allergic properties.

As employed above and throughout the disclosure, the following terms, unless otherwise indicated, shall be understood to have the following meanings:

"Alkyl", either alone or with various substituents defined herein, means a saturated aliphatic hydrocarbon, either branched or straight chained. A "loweralkyl" is preferred having about 1 to about 6 carbon atoms. Examples of alkyl include methyl, ethyl, n-propyl, isopropyl, butyl, sec-butyl, t-butyl, amyl, hexyl, etc.

"Alkoxy" refers to a loweralkyl-O-group.

"Alkenyl" refers to a hydrocarbon having at least one point of unsaturation and may be branched or straight chained. Preferred alkenyl groups have six or less carbon atoms and include vinyl, allyl, ethynyl, isopropenyl, etc.

"Aralkyl" means an alkyl group substituted by an aryl radical. The preferred aralkyl groups are benzyl or phenethyl.

"Cycloalkyl" means a saturated monocyclic hydrocarbon ring having 3 to about 6 carbon atoms. Preferred groups include cyclopropyl, cyclohexyl, etc.

"Acyl" means an organic radical derived from an organic acid by removal of its hydroxyl group. Preferred acyl groups are groups derived from carboxylic acids. More preferred are the lower alkanoyl or benzoyl groups such as acetyl, propionyl benzoyl, etc.

"Halo" means a halogen. Preferred halogens include, chloride, bromide and fluoride. The preferred haloalkyl group is trifluromethyl.

The compounds of this invention may be prepared in segments as is common to a long chain molecule. Thus it is convenient to synthesize these molecules by employing condensation reactions at the A, B and D cites of the molecule. For this reason the present compounds may be prepared by art recognized procedures from known compounds or readily preparable intermediates. Exemplary general procedures are as follows and are shown where R, R', $R_1$ and $R_2$ are all hydrogen; b, d, and e are 0; a, c, and f are 1; or b, c, e and f are 0 and a and d are 1. B is O, S or $NR_1$ and Z is $-CN$, $-COOR_1$ or tetrazolyl. Thus, in order to prepare the compound of the below formula

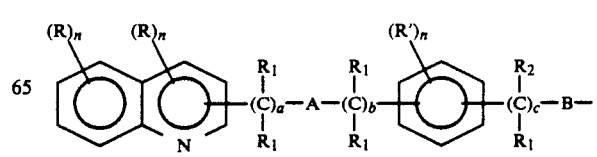

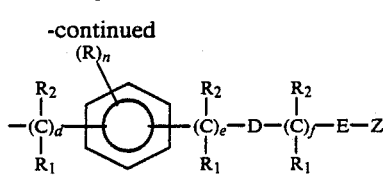

the following reactions or combinations of reactions may be employed:

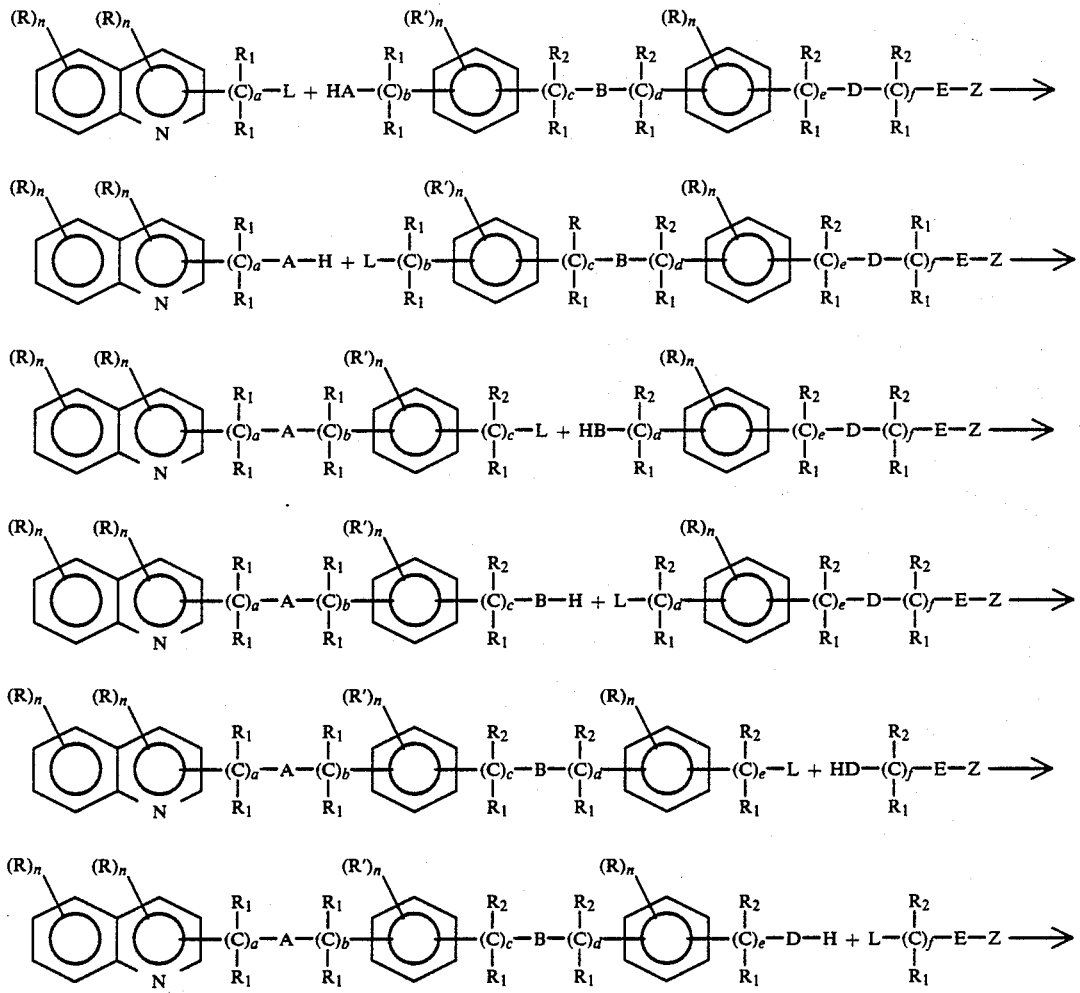

where:
R, R', R$_1$, R$_2$, a, b, c, d, e, f, n, A, and D are as defined above, B is O or S; E is a chemical bond; Z is —CN, —COOR$_1$ or tetrazolyl, and L is a leaving group, such as halo, tosylate, or mesylate. Where B is O or S, any base normally employed to deprotonate an alcohol or thiol may be used, such as sodium hydride, sodium hydroxide, triethyl amine, sodium bicarbonate or diisopropyl/ethylamine.

Reaction temperatures are in the range of room temperature to reflux and reaction times vary from 2 to 96 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

In the case where B is SO or SO then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating with 30% H$_2$O$_2$.

These compounds where B is

may be prepared by the following reaction sequence;

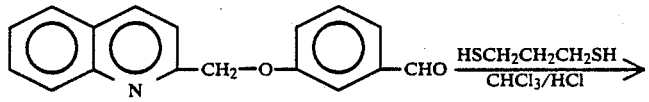

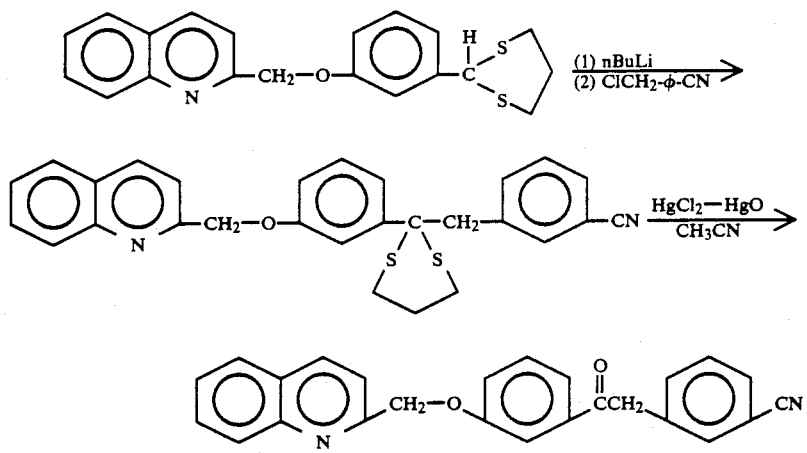

Condensation of the aldehyde with 1,3-propanedithiol results in the dithiane compound. This may be carried out in chloroform at reduced temperatures (−20° C.) while bubbling HCl gas into the reaction mixture. The dithiane compound is then treated with N-butyl lithium in nonpolar solvent at −78° C. and then reacted with the substituted benzyl chloride. This results in addition of the Ring III to the molecule. The dithiane moiety is then treated with a mercuric chloride-mercuric oxide mixture to form the complex which is then split off leaving the desired compound.

Those compounds where D and/or E are

are prepared by reacting the appropriate aldehyde or ketone with a substituted Wittig reagent of the formula

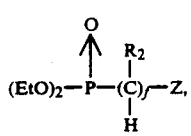

where Z is cyano or carbalkoxy.

The tetrazole may be formed from the nitrile at various stages of the synthesis by treatment with hydrazoic acid formed in situ from sodium azide and an acid.

When B is

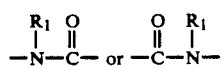

then condensation of the acid halide with the appropriate aniline will give the desired compound as shown below in the following scheme.

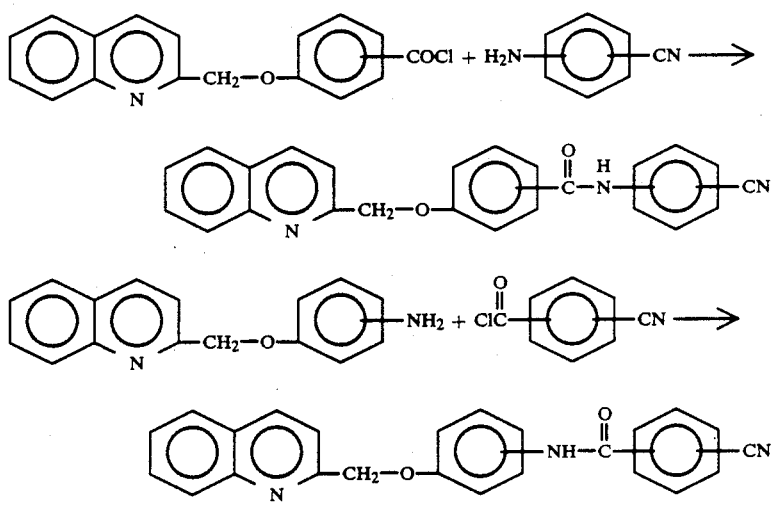

The products of this invention may be obtained as racemic mixtures of their dextro and levorotatory isomers since at least one asymmetric carbon atom may be present. When two asymmetric carbon atoms are present the product may exist as a mixture of two diastereomers based on syn and anti configurations. These diastereomers may be separated by fractional crystallization. Each diastereomer may then be resolved into dextro and levorotatory optical isomers by conventional methods.

Resolution may best be carried out in the intermediate stage where it is convenient to combine the racemic compound with an optically active compound by salt formation, ester formation, or amide formation to form two diasteromeric products. If an acid is added to an optically active base, then two diastereomeric salts are produced which possesses different properties and different solubilities and can be separated by fractional crystallization. When the salts have been completely separated by repeated crystallization, the base is split off by acid hydrolysis and the pure d and l acids are obtained.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are pharamaceutically acceptable. Basic salts for pharmaceutical use are the Na, K Ca and Mg salts.

Various substituents on the present new compounds, e.g., as defined in R, $R_1$ and $R_2$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added to the aromatic ring by nitration and the nitro group converted to other groups, such as amino by reduction, and halo by diazotization of the amino group and replacement of the diazo group. Acyl groups can be substituted onto the aryl groups by Friedel-Crafts acylation. The acyl groups can then be transformed to the corresponding alkyl groups by various methods, including the Wolff-Kishner reduction and Clennenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The compounds of the present invention have potent activity as leukotriene antagonists and as such possess therapeutic value in the treatment of inflammatory conditions and allergic responses such as anaphlaxis and asthma.

Protocol for SRS-A (slow reacting substance of anaphylaxis) Antagonist

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. This protocol describes an in vitro assay used to test compounds which specifically antagonize the actions of leukotrienes.

Peripheral strips of guinea pig lungs are prepared and hung in tissue baths (Metro #ME-5505, 10 ml) according to the published procedure — (Proc. Nat'l. Acad. Sci., U.S.A. Volume 77, pp. 4354–4358, 1980). The strips are thoroughly rinsed in Assay Buffer and then connected with surgical silk thread support rods from the tissue baths. The rods are adjusted in the baths and the strips connected to the pressure transducers (Grass FT 103 or Gould US-3). The tissue baths are aerated with 95% oxygen — 5% carbon dixoide and maintained at 37° C. The assay buffer has been made as follows: for each liter of buffer the following are added to approximately 800 ml of water distilled in glass-6.87 g NaCl, 0.4 g $MgSO_4 \cdot 7H_2O$, and 2.0 g D-glucose. Then a solution of 0.368 g $CaCl_2 \cdot H_2O$ in 100 ml glass-distilled water is slowly added to the buffer. Sufficient water is added to adjust the volume to 1 liter, and the solution is aerated with 95% oxygen — 5% carbon dioxide. Usually 10 liters of buffer are used for an experiment with 4 tissues. After the tissues have been repeatedly washed and allowed to equilibrate in the tissue bath, they are challenged with 1 $\mu M$ histamine. After maximum contractions have been obtained, the tissues are washed, and allowed to relax back to baseline tension. This histamine challenge procedure is repeated at least 1 to 2 more times to obtain a repeatable control response. The average response to 1 $\mu M$ histamine for each tissue is used to normalize all other challenges.

Responses of each tissue to a predetermined concentration of leukotriene are then obtained. Usually test compounds are examined initially at 30 $\mu M$ on resting tension of the tissues without any added agonist or antagonist to determine if the compound has any possible intrinsic activity. The tissues are washed and the test compound is added again. Leukotriene is added after the desired pre-incubation time. The intrinsic activity of the compounds, and their effect on leukotriene-induced contractions are then recorded.

The results of this test for the compounds of the this invention indicates that these comopunds are considered to be useful leukotriene antagonists.

Inhibition of ($^3H$)-$LTD_4$ Binding Membranes from Guinea Pig Lung.

A. Preparation of the Crude Receptor Fraction

This procedure was adapted from Mong et al (1984). Male guinea pigs are sacrificed by decapitation and their lungs are quickly removed and placed in a beaker containing ice-cold homogenization buffer. The lungs are separated from connective tissue, minced with scissors, blotted dry and weighed. The tissue is then homogenized in 40 volumes (w/v) of homogenization buffer with a Polytron at a setting of 6 for 30 seconds. The homogenate is centrifuged at 1000×g for 10 minutes (e.g. 3500 RPM, SS-34 Rotor). The supernate is filtered through two layers of cheese cloth and centrifuged at 30,000×g for 30 minutes (e.g. 18,500 RPM SS-34 Rotor), after which the resulting pellet is resuspended in 20 volumes of assay buffer by hand homogenization using a Dounce homogenizer. The final pellet is resuspended in 10 volumes of assay buffer and kept at 4° C. until use.

B. Binding Assay

Each assay tube (16×100 mm) contains the following:

490 $\mu L$ Assay Buffer
10 $\mu L$ Test compound or solvent
100 $\mu L$ $^3H$-$LTD_4$ (ca. 17,500 DMP)
400 $\mu L$ Protein preparation Incubations are done at 25° C. for 20 minutes in a shaking water bath. Reactions are started by the addition of the protein preparation. At the end of the incubation time, 4.0 ml of cold wash buffer is added to the tube. After being vortexed, the contents of the tube are immediately poured over a Whatman GF/C Filter (25 mm diameter) which is sitting in a vacuum manifold (e.g., Millipore Model No. 3025 manifold) to which a partial vacuum is applied. The filters are immediately washed with an additional 15 ml of cold buffer. The filter are transferred to 7 ml plastic scintillation vials to which 6.0 ml of appropriate scintillation fluid (e.g., Scintiverse) is added. After being allowed to equilibrate for 4-6 hours, the radioactivity is counted with a liquid scintillation counter appropriately set for tritium.

The required control assay tubes include the following:

(a) Total Binding: No test compound is added; buffer is substituted.

(b) Non-Specific Binding: Non-labeled ligand is added at a concentration of 1 $\mu M$.

(c) Solvent Controls: If test compound is dissolved in a solvent, controls for both Total Binding and Non-Specific Binding containing solvent but no compounds are required.

The results of this test indicate that the compounds of this invention exhibit valuable properties which are useful in the treatment of inflammatory conditions and allergic responses.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amount employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably nixed with a surfactant such as hydroxypropyl-cellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administer-ed to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 mM/day or from about 0.1 mg to about 50 mg/kg of body weight per day and higher although it may be administered in several different dosage units. Higher dosages are required for oral administration.

The compounds of the present invention may be prepared by the following representative examples.

EXAMPLE 1

3-(2-Quinolinylmethyloxy)Benzyl Alcohol

A mixture of 12.8 g (0.06 mol) of 2-quinolinylmethyl chloride HCl, 7.5 g (0.06 mol) of 3-hydroxybenzyl alcohol, and 18 g of potassium carbonate in 50 ml of DMF is heated at 70° C. overnight. The reaction mixture is poured into water, and the precipitated product is collected, filtered and dried to give 3-(2-quinolinylmethyloxy)benzyl alcohol.

EXAMPLE 2

When 2-quinolinylmethyl chloride of Example 1 above is replaced by the quinoline compounds of Table I below then the corresponding product is obtained.

TABLE I 2-chloromethylquinoline
2-bromomethylquinoline
2-(1-chloroethyl)quinoline
2-(2-chloroethyl)quinoline
2-bromoethylquinoline
3-chloromethylquinoline
4-chloromethylquinoline
2-(β-chloroethyl)quinoline
2-(β-chloropropyl)quinoline
2-(β-chloro-β-phenethyl)quinoline
2-chloromethyl-4-methylquinoline
2-chloromethyl-6-methylquinoline
2-chloromethyl-8-methylquinoline
2-chloromethyl-6-methoxyquinoline
2-chloromethyl-6-nitroquinoline
2-chloromethyl-6,8-dimethylquinoline

EXAMPLE 3

When 3-hydroxybenzyl alcohol of Example 1 above is replaced by the compounds of Table II below then the corresponding product is obtained.

TABLE II 1,2-benzenediol
1,3-benzenediol
1,4-benzenediol
2-mercaptophenol
3-mercaptophenol
4-mercaptophenol
1,3-dimercaptobenzene
1,4-dimercaptobenzene
3-hydroxybenzyl alcohol
3-hyroxyethylphenol
4-hydroxybenzyl alcohol
4-hydroxyethylphenol
2-methylresorsinol
5-methylresorsinol
5-methoxyresorsinol
5-methyl-1,4-dihydroxybenzene
3-(N-acetylamino)phenol
3-(N-acetylamino)benzyl alcohol
2-hydroxy-α-methylbenzyl alcohol
2-hydroxy-α-ethylbenzyl alcohol
2-hydroxy-α-propylbenzyl alcohol
3-hydroxy-α-methylbenzyl alcohol
3-hydroxy-α-ethylbenzyl alcohol
3-hydroxy-α-propylbenzyl alcohol
4-hydroxy-α-methylbenzyl alcohol
4-hydroxy-α-ethylbenzyl alcohol
4-hydroxy-α-propylbenzyl alcohol

EXAMPLE 4

When the compounds of Table I, Example 2 are reacted with the compounds of Table II, Example 3 under the conditions of Example 1 then corresponding products are obtained.

EXAMPLE 5

3-(2-Quinolinylmethyloxy)Benzyl Chloride

To a stirred solution of 14.5 g of 3-(2-quinolinylmethyloxy)benzyl alcohol in 150 ml of CHCl3 is added dropwise 7.5 ml of thionyl chloride during 10 min. The reaction mixture is stirred for 4 hours at room temperature, and then washed with NaHCO3 solution. The organic solution is separated, dried, and evaporated to give 3-(2-quinolinylmethyloxy)benzyl chloride which is used without further purification in the next step.

EXAMPLE 6

When the compounds prepared by Examples 2–4 are used in place of 3-(2-quinolinymethyloxy)benzyl alcohol in Example 5, then the corresponding chloride is prepared.

EXAMPLE 7

3-[3-(2-Quinolinylmethyloxy)benzyloxy]Benzonitrile

A solution of 0.65 g (5.4 mmol) 3-hydroxybenzoinitirle, 1.5 g (5.3 mmol) of 3-(2-quinolinylmethyloxy)benzyl chloride, and 0.75 g (5.4 mmol) of potassium carbonate in 15 ml of DMF is heated at 60° C. overnight. The reaction mixture is poured into water. The precipitated product is collected on a filter and purified by dry column chromatography to give 3-[3-(2-quinolinylmethyloxy)benzyloxy]benzonitrile. (M.P. 86°–87° C.)

EXAMPLE 8

When 3-hydroxybenzonitrile of Example 7 above is replaced by the compounds of Table III below then the corresponding product is obtained. cl TABLE III 2-hydroxybenzonitrile
3-hydroxybenzonitrile
4-hydroxybenzonitrile
2-cyanomethylphenol
3-cyanomethylphenol
4-cyanomethylphenol
2-cyanoethylphenol
3-cyanoethylphenol
4-cyanoethylphenol
2-cyanoethylphenol
3-cyanopropylphenol
4-cyanopropylphenol 2-cyanopropylphenol
3-cyanobutylphenol
4-cyanobutylphenol
2-methyl-3-hydroxybenzonitrile
4-methyl-3-hydroxybenzonitrile
5-methyl-3-hydroxybenzonitrile
2-methyl-4-hydroxybenzonitrile
3-methyl-4-hydroxybenzonitrile
5-methyl-4-hydroxybenzonitrile
4-methoxy-3-hydroxybenzonitrile
3-methoxy-4-hydroxybenzonitrile
2-methoxy-4-hydroxybenzonitrile
2-methoxy-4-hydroxybenzonitrile
4-carbomethoxy-3-hydroxybenzonitrile
5-carbomethoxy-3-hydroxybenzonitrile
3-carbomethoxy-4-hydroxybenzonitrile
2,5-dimethyl-4-hydroxybenzonitrile
3-methyl-4-cyanomethylphenol
2-methyl-4-cyanomethylphenol
2-methyl-3-cyanomethylphenol
4-methyl-3-cyanomethylphenol
5-methyl-3-cyanomethylphenol
2-mercaptobenzonitrile
3-mercaptobenzonitrile
4-mercaptobenzonitrile
3-mercaptobenzylnitrile
4-mercaptobenzylnitrile
4-methyl-3-mercaptobenzonitrile
2-cyanomethyl-1-hydroxymethylbenzene
3-cyanomethyl-1-hydroxymethylbenzene
4-cyanomethyl-1-hydroxymethylbenzene
2-hydroxymethylbenzonitrile
3-hydroxymethylbenzonitrile
4-hydroxymethylbenzonitrile
3-(N-acetylamino)benzonitrile
4-(N-acetylamino)benzonitrile

EXAMPLE 9

When the compounds of Example 6 are used in place of 3-(2-quinolinylmethyloxy)benzyl chloride in Examples 7 and 8 then the corresponding nitriles are obtained.

EXAMPLE 10

5-[3-(3-(2-Quinolinylmethyloxy)benzyloxy)Phenyl]Tetrazole

A mixture of 1.2 g (3.28 mmol) of 3-[3-(2-quinolinylmethyloxy)benzyloxy]benzonitrile, 1.89 g (16.4 mmol) of pyridine hydrochloride, and 1.06 g (16.4 mmol) of sodium azide in 10 ml of DMF is heated at 100° C. for 4 days. The reaction mixture is poured into water. The crude product collected on a filter and recrystallized from ethyl acetate to give 5-['-(3-(2-quinolinylmethyloxy)benzyloxy)phenyl]tetrazole. (M.P. 169°-172° C.)

EXAMPLE 11

When 4-hydroxybenzyl alcohol is used in place of 3-hydroxybenzyl alcohol in Example 1 and 4-hydroxybenzonitrile is used in place of 3-hydroxybenzonitrile in Example 7 then the product obtained is 5-[4-(4-(2-quinolinylmethyloxy)benzyloxy)phenyl]tetrazole. (M.P. 210°-213° C.)

EXAMPLE 12

When 4-cyanomethylphenol is used in place of 4-hydroxybenzonitrile in Example 11 then the product obtained is 5-[4-(4-(2-quinolinylmethyloxy)benzyloxy)benzyl]tetrazole. (M.P. 179°-181° C.)

EXAMPLE 13

When the nitrile compounds of Example 9 are used in place of 3-[3-(2-quinolinylmethyloxy)benzyloxy]benzonitrile in Example 10 of corresponding tetrazole product is obtained. Representative examples of compounds obtained by this invention are shown in Table IV below.

TABLE IV

5-[3-(4-(2-quinolinylmethyloxy)benzyloxy)phenyl]tetrazole
5-[2-(4-(2-quinolinylmethyloxy)benzyloxy)phenyl]tetrazole
5-[4-(3-(2-quinolinylmethyloxy)benzyloxy)phenyl]tetrazole
5-[4-(2-(2-quinolinylmethyloxy)benzyloxy)phenyl]tetrazole
5-[2-(3-(2-quinolinylmethyloxy)benzyloxy)phenyl]tetrazole
5-[3-(3-(2-quinolinylmethyloxy)benzyloxy)benzyl]tetrazole
5-[4-(3-(2-quinolinylmethyloxy)benzyloxy)benzyl]tetrazole
5-[3-(4-(2-quinolinylmethyloxy)benzyloxy)benzyl]tetrazole
5-[2-(3-(2-quinolinylmethyloxy)benzyloxy)benzyl]tetrazole
5-[4-(2-(2-quinolinylmethyloxy)benzyloxy)benzyl]tetrazole
5-[2-(4-(2-quinolinylmethyloxy)benzyloxy)benzyl]tetrazole
5-[2-(3-(4(2-quinolinylmethyloxy)benzyloxy)phenyl)-propyl]tetrazole
5-[2-(3-(4(2-quinolinylmethyloxy)benzyloxy)phenyl)-butyl]tetrazole
5-[3-(3-(4(2-quinolinylmethyloxy)benzyloxy)phenyl)-butyl]tetrazole
5-[3-(3-(2-quinolinylmethylthio)benzyloxy)phenyl]tetrazole
5-[3-(3-(2-quinolinylmethylthio)benzylthio)phenyl]tetrazole
5-[3-(3-(2-quinolinylmethyloxy)benzylthio)phenyl]tetrazole
5-[4-(3-(2-quinolinylmethyloxy)benzyloxy)-3-methoxyphenyl]tetrazole
5-[3-(3-(2-quinolinylmethyloxy)benzyloxy)-4-methoxyphenyl]tetrazole
5-[4-(4-(2-quinolinylmethyloxy)benzyloxy)-3-methoxyphenyl]tetrazole
5-[3-(4-(2-quinolinylmethyloxy)benzyloxy)-4-methoxyphenyl]tetrazole
5-[4-(3-(2-quinolinylmethyloxy)benzyloxy)-2-methoxyphenyl]tetrazole
5-[4-(3-(2-quinolinylmethyloxy)benzyloxy)-3-carbomethoxyphenyl]tetrazole
5-[4-(3-(2-quinolinylmethyloxy)benzyloxy)-3-methoxybenzyl]tetrazole
5-[4-(4-(2-quinolinylmethyloxy)benzyloxy)-3-methoxybenzyl]tetrazole
5-[4-(4-(2-quinolinylmethyloxy)benzyloxy)-3-carbomethoxybenzyl]tetrazole
5-[4-(3-(2-quinolinylmethyloxy)benzyloxy)-3-carbomethoxybenzyl]tetrazole
5-[4-(3-(2-quinolinylmethyloxy)benzylthio)phenyl]tetrazole 5-[3-(4-(2-quinolinylmethyloxy)benzylthio)phenyl]tetrazole
5-[4-(3-(2-quinolinylmethyloxy)-N-acetyl-benzylamino)phenyl]tetrazole
5-[4-(4-(2-quinolinylmethyloxy)-N-acetyl-benzylamino)phenyl]tetrazole

EXAMPLE 14

Methyl 3-Methoxy-4-[3-(2-Quinolinylmethyloxy)Benzyloxy]-Benzoate

A mixture of 3 g of 3-(2-quinolinylmethyloxy) benzyl chloride, 1.93 g of methyl 4-hydroxy-3-methoxy benzoate, and 1.5 g of potassium carbonate in 30 ml of DMF is heated at 50° overnight. The reaction mixture is poured into water, the solid product collected on a filter and purified by dry column chromatography to give methyl 3-methoxy-4-(3-(2-quinolinylmethyloxy)benzyloxy)-benzoate. (M.P. 100°–101° C.)

EXAMPLE 15

3-Methoxy-4-[3-(2-Quinolinylmethyloxy)Benzyloxy]-Benzoic Acid

A mixture of 2.6 g of methyl 3-methoxy-4-[3-(2-quinolinylmethyloxy)benzyloxy]benzoate and 0.6 g of NaOH in 15 ml of THF and 2 ml of H2O are heated at 60° C. overnight. The reaction mixture is diluted with 20 ml of HO and acidified to pH 4. The product is collected on a filter and dried to give 3-methoxy-4-(3-(2-quinolinylmethyloxy)benzyloxy)benzoic acid. (M.P. 188°–190° C.)

EXAMPLE 16

When methyl 4-hydroxy-3-methoxybenzoate is replaced in the procedure of Example 14 with the compounds of Table V, below, then the corresponding products are obtained. Representative examples of compounds prepared by this invention are shown in Table VI.

TABLE V methyl 2-hydroxybenzoate
methyl 3-hydroxybenzoate
methyl 4-hydroxybenzoate
methyl 4-hydroxy-3-methoxybenzoate
methyl 3-hydroxy-4-methoxybenzoate
methyl 4-hydroxy-2-methoxybenzoate
methyl 3-hydroxy-4-methoxybenzoate
ethyl 4-hydroxy-3-ethoxybenzoate
methyl 4-hydroxy-3-methylbenzoate
methyl 3-hydroxy-4-methylbenzoate
methyl 4-hydroxy-2-methylbenzoate
methyl 3-hydroxy-4-methylbenzoate
methyl 4-hydroxy-2,6-dimethylbenzoate
methyl 4-hydroxy-2,5-dimethylbenzoate
methyl 2-hydroxyphenylacetate
methyl 3-hydroxyphenylacetate
methyl 4-hydroxyphenylacetate
methyl 4-hydroxyphenylpropionate
methyl 4-hydroxyphenylbutyrate
methyl 4-hydroxyphenyl-3'-methylbutyrate
methyl 4-hydroxy-3-methylphenylacetate
methyl 3-hydroxy-4-methylphenylacetate
methyl 4-hydroxy-3-methoxyphenylacetate
methyl 3-hydroxy-4-methoxyphenylacetate
methyl 2-hydroxymethylbenzoate
methyl 3-hydroxymethylbenzoate
methyl 4-hydroxymethylbenzoate
methyl 2-hydroxymethylphenylacetate
methyl 3-hydroxymethylphenylacetate
methyl 4-hydroxymethylphenylacetate
3-mercaptobenzoate
4-mercaptobenzoate
3-mercaptomethylbenzoate
3-(N-acetylamino)benzoate
4-(N-acetylamino)benzoate
4-(N-benzylamino)benzoate

TABLE VI 4-(3-(2-quinolinylmethyloxy)benzyloxy)benzoic acid
4-(4-(2-quinolinylmethyloxy)benzyloxy)benzoic acid
3-(4-(2-quinolinylmethyloxy)benzyloxy)benzoic acid
3-(3-(2-quinolinylmethyloxy)benzyloxy)benzoic acid
2-(4-(2-quinolinylmethyloxy)benzyloxy)benzoic acid
4-(3-(2-quinolinylmethyloxy)benzyloxy)phenylacetic acid
4-(3-(2-quinolinylmethyloxy)phenoxy)benzoic acid
4-(3-(2-quinolinylmethyloxy)benzyloxymethyl)benzoic acid
3-methyl-4-(3-(2-quinolinylmethyloxy)benzyloxy)benzoic acid
4-methyl-3-(3-(2-quinolinylmethyloxy)benzyloxy)benzoic acid
2-methyl-4-(3-(2-quinolinylmethyloxy)benzyloxy)benzoic acid
3-methoxy-4-(3-(2-quinolinylmethyloxy)benzyloxy)-benzoic acid
4-methoxy-3-(3-(2-quinolinylmethyloxy)benzyloxy)-benzoic acid
2,6-dimethyl-4-(3-(2-quinolinylmethyloxy)benzyloxy)-benzoic acid
4-(3-(2-quinolinylmethyloxy)benzylthio)benzoic acid
4-(3-(2-quinolinylmethyloxy)benzylamino)benzoic acid

EXAMPLE 17

3-Methoxy-4-(3-(2-Quinolinylmethyloxy) Benzyloxy)Benzoyl-N-Benzenesulfonamide

A reaction mixture of 0.73 g of 3-methoxy-4-(3-(2-quinolinyl-methyloxy)benzyloxy)benzoic acid, 0.28 g of benzenesulfonamide, 0.28 g of 4-dimethylpyridine, and 0.44 g of 1-(3-dimethylamino-propyl)-3-ethylcarbodiimide hydrochloride in 50 ml of CH2Cl2 is stirred at room temperature overnight. The solvent is removed and the residue is extracted into ethyl acetate. The organic solution is washed with water, and evaporated. The product is purified by dry column chromatography to give 3-methoxy-4-(3-(2-quinolinylmethyloxy)benzyloxy)benzoyl-N-benzenesulfonamide. (M.P. 156°–158° C.)

EXAMPLE 18

When 3-methoxy-4-(3-(2-quinolinylmethyloxy)benzyloxy)benzoic acid of Example 17 is replaced by the acids of this invention such as those of Example 16, Table VI and Example 25, Table IX then the corresponding benzenesulfonamide compound is prepared.

When benzenesulfonamide is replaced in the above Examples by a sulfonamide of the formula $NH_2SO_2R_3$ or an amine of the formula $HN(R_1)_2$, then the corresponding product is obtained.

EXAMPLE 19

Methyl 3-(3-(2-Quinolinylmethyloxy)Phenoxymethyl)Benzoate

A mixture of 3-(2-quinolinylmethyloxy)phenol (2.51 g, 0.01 mol), 1.85 g (0.01 mol) of methyl 3-chloromethyl benzoate, and 1.5 g of potassium carbonate in 30 ml of DMF is heated at 50° C. overnight. The reaction mixture is poured into water, extracted with ethyl acetate and the organic solution separated, dried and evaporated to dryness. Recrystallization from ethyl acetate gives methyl 3-(3-(2-quinolinylmethyloxy)phenoxymethyl)benzoate. (M.P. 93°-94° C.)

EXAMPLE 20

A mixture of 1.6 g of methyl 3-(3-(2-quinolinylmethyloxy)phenoxymethyl)benzoate and 0.5 g of NaOH in 20 ml of THF and 5 ml of H2O is heated at 50° C. overnight. The reaction mixture is acidified to pH 4 in 1N HCl solution, filtered and dried to give 3-(3-(2-quinolinylmethyloxy)phenoxymethyl)benzoic acid. (M.P. 149°-151° C.)

EXAMPLE 21

When the procedures of Examples 19 and 20 are followed and methyl 3-chloromethylbenzoate is replaced by methyl 4-chloromethylbenzoate, then the product prepared is 4-(3-(2-quinolinylmethyloxy)-phenoxymethyl)benzoic acid. (M.P. 190°-191° C.)

EXAMPLE 22

When the procedures of Examples 19 and 20 are followed and methyl 3-chloromethylbenzoate is replaced by methyl 3-methoxy-4-chloromethylbenzoate then the product prepared is 3-methoxy-4-(3-(2-quinolinylmethyloxy)phenoxymethyl)benzoic acid. (M.P. 208°-210° C.)

EXAMPLE 23

When the procedure of Example 19 is followed and the compounds of Table VII below are used in place of methyl 3-chloromethyl-benzoate then the corresponding product is obtained.

TABLE VII ethyl 2-chloromethylbenzoate
ethyl 3-chloromethylbenzoate
ethyl 4-chloromethylbenzoate
ethyl 3-chloromethylbenzoate
methyl 4-chloromethylbenzoate
methyl 2-methyl-5-chloromethylbenzoate
methyl 2-methyl-3-chloromethylbenzoate
methyl 3-methyl-5-chloromethylbenzoate
methyl 4-methyl-5-chloromethylbenzoate
methyl 2-methyl-4-chloromethylbenzoate
methyl 3-methyl-4-chloromethylbenzoate
methyl 2-methoxy-5-chloromethylbenzoate
methyl 2-methoxy-3-chloromethylbenzoate
methyl 2-methoxy-4-chloromethylbenzoate
methyl 3-methoxy-4-chloromethylbenzoate
methyl 3-chloromethylphenylacetate
methyl 4-chloromethylphenylacetate
methyl 3-chloromethylphenylpropionate
methyl 4-chloromethylphenylpropionate
methyl 3-chloromethylphenylbutyrate
methyl 4-chloromethylphenylbutyrate
methyl 3-chloromethylphenylisopropionate
methyl 4-chloromethylphenylisopropionate
methyl 3-chloromethylphenylisopropionate
methyl 4-chloromethylphenylisobutyrate

EXAMPLE 24

When the procedure of Example 19 is followed and the compound of Table VIII below are used in place of 3-(2-quinolinyl-methyloxy)phenol then the corresponding product is obtained.

TABLE VIII 3-(2-quinolinylmethyloxy)phenol
4-(2-quinolinylmethyloxy)phenol
3-(2-quinolinylmethylthio)phenol
4-(2-quinolinylmethylthio)phenol
5-methyl-3(2-quinolinylmethyloxy)phenol
2-methyl-3(2-quinolinylmethyloxy)phenol
5-methoxy-3(2-quinolinylmethyloxy)phenol
2-methyl-4-(2-quinolinylmethyloxy)phenol
2-methoxy-4-(2-quinolinylmethyloxy)phenol
3-methoxy-4-(2-quinolinylmethyloxy)phenol
3-methyl-4-(2-quinolinylmethyloxy)phenol
3-(2-quinolinylmethyloxy)phenol mercaptan
4-(quinolinylmethyloxy)phenol mercaptan
3-(2-quinolinylmethylthio)phenyl mercaptan
4-(2-quinolinylmethylthio)phenol mercaptan
N-benzyl-3-(2-quinolinylmethyloxy)phenylamine
N-methyl-3-(2-quinolinylmethyloxy)phenylamine
N-acetyl-3-(2-quinolinylmethyloxy)phenylamine
N-acetyl-4-(2-quinolinylmethyloxy)phenylamine

EXAMPLE 25

When the procedures of Examples 19 and 20 are followed using the compounds of Table VII, Example 23 and Table VIII, Example 24, then the corresponding product is obtained. Representative examples of compounds prepared by this invention are shown in Table IX.

TABLE IX 3-(4-(2-quinolinylmethyloxy)phenoxymethyl)benzoic acid
4-(4-(2-quinolinylmethyloxy)phenoxymethyl)benzoic acid
2-(3-(2-quinolinylmethyloxy)phenoxymethyl)benzoic acid
2-(4-(2-quinolinylmethyloxy)phenoxymethyl)benzoic acid
2-methyl-3-(3-(2-quinolinylmethyloxy)phenoxymethyl)benzoic acid
2-ethyl-3-(3-(2-quinolinylmethyloxy)phenoxymethyl)benzoic acid
2-methoxy-3-(3-(2-quinolinylmethyloxy)phenoxymethyl)benzoic acid
3-methyl-4-(3-(2-quinolinylmethyloxy)phenoxymethyl)benzoic acid
2-methyl-4-(3-(2-quinolinylmethyloxy)phenoxymethyl)benzoic acid
2-methoxy-4-(3-(2-quinolinylmethyloxy)phenoxymethyl)benzoic acid
3-(3-(2-quinolinylmethyloxy)-5-methylphenoxymethyl)benzoic acid
3-(3-(2-quinolinylmethyloxy)-5-methoxyphenoxymethyl)benzoic acid
3-(4-(2-quinolinylmethyloxy)-3-methylphenoxymethyl)benzoic acid
3-(4-(2-quinolinylmethyloxy)-2-methylphenoxymethyl)benzoic acid 2-methyl-3-(3-(2-quinolinylmethyloxy)-2-methyl-phenoxymethyl)benzoic acid
3-(3-(2-quinolinylmethylthio)phenoxymethyl)benzoic acid
4-(4-(2-quinolinylmethylthio)phenoxymethyl)benzoic acid
3-(3-(2-quinolinylmethyloxy)phenoxymethyl)phenylacetic acid
3-(3-(2-quinolinylmethyloxy)phenoxymethyl)phenylpropionic acid
3-(3-(2-quinolinylmethyloxy)phenylthiomethyl)benzoic acid
4-(3-(2-quinolinylmethyloxy)phenylthiomethyl)benzoic acid
3-(4-(2-quinolinylmethyloxy)phenylthiomethyl)benzoic acid
3-(3-(2-quinolinylmethyloxy)phenyl-N-acetylaminomethyl)benzoic acid
4-(4-(2-quinolinylmethyloxy)phenyl-N-acetylaminomethyl)benzoic acid

EXAMPLE 26

4-(3-(2-Quinolinylmethyloxy)Phenoxymethyl)Benzonitrile

A solution of 7.24 g (19.92 mmol) of sodium 3-(2-quinolinylmethyloxy)phenoxide pentahydrate and 4.68 g (23.90 mmol) of p-cyanobenzyl bromide in 34 ml of dry DMF is stirred at 75° C. under nitrogen for 2 days. The reaction mixture is cooled to room temperature, then poured into 400 ml of 3:1 H$_2$O/Et$_2$O, shaken, and the phases separated. The aqueous layer is extracted and washed with 1:1 brine/H$_2$O and brine. The ether solution is dried over 1:1 Na$_2$SO$_4$MgSO$_4$, filtered and concentrated. The crude product is recrystallized from 70% EtOAc/hexane to obtain 4-(3-(2-quinolinylmethyloxy)phenoxy-methyl)benzonitrile. (M.P. 112.5° C.)

EXAMPLE 27

5-(4-(3-(2-Quinolinylmethyloxy)Phenoxymethyl)-Phenyl)Tetrazole

A slurry of 2.0 g (5.48 mmol) of 4-(3-(2-quinolinylmethyloxy)phenoxymethyl)benzonitrile, 1.78 g (27.4 mmol) of sodium azide, and 3,16 g (27.4 mmol) of pyridinium hydrochloride in 12 ml of dry DMF is stirred under nitrogen at 100° C. for 20 hrs. The reaction mixture is then cooled to room temperature and concentrated. The residue is taken up on 100 ml of 1N aqueous NaOH and the solution extracted with ether. The aqueous layer is acidified to pH 6 with 1N aqueous HCl, and the precipitate collected, triturated with water, filtered and lyophilized to obtain 5-(4-(3-(2-quinolinylmethyloxy)phenoxymethyl)phenyl)tetrazole (M.P. 91° C. dec.)

EXAMPLE 28

When the procedures of Examples 26 and 27 are followed and p-cyanobenzyl bromide is replaced by o-cyanobenzyl bromide, m-cyanobenzyl bromide, o-(cyanomethyl)benzyl bromide, m-(cyanomethyl)benzyl bromide, p-(cyanomethyl)-benzyl bromide, then the products prepared are:
5-(2-(3-(2-quinolinylmethyloxy)phenoxymethyl)-phenyl)tetrazole (M.P. 166°-170° C.);
5-(3-(3-(2-quinolinylmethyloxy)phenoxymethyl)-phenyl)tetrazole (M.P. 115° C. dec.);
5-(2-(3-(2-quinolinylmethyloxy)phenoxymethyl)benzyl)tetrazole (M.P. 145.5°-147° C.);
5-(3-(3-(2-quinolinylmethyloxy)phenoxymethyl)benzyl)tetrazole (M.P. 161°-164° C.); and
5-(4-(3-(2-quinolinylmethyloxy)phenoxymethyl)benzyl)tetrazole (M.P. 149°-152° C.).

EXAMPLE 29

When the procedure of Example 26 is followed and the compounds of Table X below are used in place of p-cyanobenzyl bromide then the corresponding product is obtained.

TABLE X 2-methyl-4-cyanobenzyl bromide
3-methyl-4-cyanobenzyl bromide
3-methoxy-2-cyanobenzyl bromide
2-methyl-3-cyanobenzyl bromide
3-cyano-4-methylbenzyl bromide
4-methoxy-2-cyanobenzyl bromide
3-cyano-5-methylbenzyl bromide
2-methyl-5-cyanobenzyl bromide
2-methoxy-5-cyanobenzyl bromide
2-methoxy-4-cyanobenzyl bromide
2-methoxy-3-cyanobenzyl bromide
2,6-dimethyl-4-cyanobenzyl bromide
3-methoxy-4-cyanobenzyl bromide
2-methyl-6-cyanobenzyl bromide
o-cyanobenzyl bromide
m-cyanobenzyl bromide
p-cyanobenzyl bromide
2-cyanomethylbenzyl bromide
3-cyanomethylbenzyl bromide
4-cyanomethylbenzyl bromide
3-(1'-cyanoethyl)benzyl bromide
3-(2'-cyanoethyl)benzyl bromide
4-(1'-cyanoethyl)benzyl bromide
4-(2'-cyanoethyl)benzyl bromide
3-(1'-cyanopropyl)benzyl bromide
3-(2'-cyanopropyl)benzyl bromide
3-(3'-cyanopropyl)benzyl bromide
4-(1'-cyanopropyl)benzyl bromide
4-(2'-cyanopropyl)benzyl bromide
4-(3'-cyanopropyl)benzyl bromide
3-(1'-cyanobutyl)benzyl bromide
3-(2'-cyanobutyl)benzyl bromide
3-(3'-cyanobutyl)benzyl bromide
3-(4'-cyanobutyl)benzyl bromide
4-(1'-cyanobutyl)benzyl bromide
4-(2'-cyanobutyl)benzyl bromide
4-(3'-cyanobutyl)benzyl bromide
4-(4'-cyanobutyl)benzyl bromide
3-(2'-methyl-1'-cyanobutyl)benzyl bromide
3-(3'-methyl-1'-cyanobutyl)benzyl bromide
4-(2'-methyl-1'-cyanobutyl)benzyl bromide
4-(3'-methyl-1'-cyanobutyl)benzyl bromide

EXAMPLE 30

When the procedure of Example 26 is followed and the sodium or other appropriate salt of the alcohol or mercaptan of Table VIII, Example 24 is used is place of sodium 3-(2-quinolinylmethyloxy)-phenoxide then the corresponding product is obtained.

EXAMPLE 31

When the procedures of Examples 26 and 27 are followed using the compounds of Table X, Examples 29 and the appropriate alcohol, thio or amino salt formed in Example 30, then the corresponding products are obtained. Representative examples of compounds prepared by this invention are shown in Table XI.

TABLE XI 5-(4-(4-(2-quinolinylmethyloxy)phenoxymethyl)phenyl) tetrazole
5-(3-(4-(2-quinolinylmethyloxy)phenoxymethyl)phenyl) tetrazole
5-(3-(2-(2-quinolinylmethyloxy)phenoxymethyl)phenyl) tetrazole
5-(2-(4-(2-quinolinylmethyloxy)phenoxymethyl)phenyl) tetrazole
5-(4-(2-(2-quinolinylmethyloxy)phenoxymethyl)phenyl) tetrazole
5-(2-(2-(2-quinolinylmethyloxy)phenoxymethyl)phenyl) tetrazole
5-(3-(3-(2-quinolinylmethyloxy)phenoxymethyl)phenyl) tetrazole
5-(4-(3-(2-quinolinylmethyloxy)-5-methoxyphenoxymethyl)phenyl)tetrazole
5-(4-(3-(2-quinolinylmethyloxy)-5-methylphenoxymethyl)phenyl)tetrazole
5-(3-(4-(2-quinolinylmethyloxy)-2-methylphenoxymethyl)phenyl)tetrazole
5-(3-(4-(2-quinolinylmethyloxy)-2-methoxyphenoxymethyl)phenyl)tetrazole
5-(4-(3-(2-quinolinylmethyloxy)-2-methylphenoxymethyl)phenyl)tetrazole
5-(4-(4-(2-quinolinylmethyloxy)-2-methylphenoxymethyl)phenyl)tetrazole
5-(4-(4-(2-quinolinylmethyloxy)-3-methylphenoxymethyl)phenyl)tetrazole
5-(4-(3-(2-quinolinylmethylthio)phenoxymethyl)phenyl)tetrazole
5-(3-(3-(2-quinolinylmethylthio)phenoxymethyl)phenyl)tetrazole
5-(2-(3-(2-quinolinylmethylthio)phenoxymethyl)phenyl)tetrazole
5-(2-(4-(2-quinolinylmethyloxy)phenoxymethyl)benzyl)tetrazole
5-(4-(4-(2-quinolinylmethyloxy)phenoxymethyl)benzyl)tetrazole
5-(3-(4-(2-quinolinylmethyloxy)phenoxymethyl)benzyl)tetrazole
5-(4-(3-(2-quinolinylmethyloxy)phenoxymethyl)phenethyl)tetrazole
5-(3-(2(4-(2-quinolinylmethyloxy)phenoxymethyl)phenyl)propyl)tetrazole
5-(4-(3(2-(2-quinolinylmethyloxy)phenoxymethyl)phenyl)butyl)tetrazole
5-(2-(4-(3-(2-quinolinylmethyloxy)phenoxymethyl)phenyl)propyl)tetrazole
5-(3-(4-(3-(2-quinolinylmethyloxy)phenoxymethyl)phenyl)butyl)tetrazole
5-(4-(4-(3-(2-quinolinylmethyloxy)phenoxymethyl)phenyl)-3methylbutyl)tetrazole
5-(4-(3-(2-quinolinylmethyloxy)phenylthiomethyl)phenyl)tetrazole
5-(4-(3-(2-quinolinylmethylthio)phenylthiomethyl)phenyl)tetrazole
5-(4-(3-(2-quinolinylmethyloxy)phenoxymethyl)-3-methylphenyl)tetrazole
5-(4-(3-(2-quinolinylmethyloxy)phenoxymethyl)-2-methylphenyl)tetrazole
5-(4-(3-(2-quinolinylmethyloxy)phenoxymethyl)-2-methoxyphenyl)tetrazole
5-(4-(3-(2-quinolinylmethyloxy)phenoxymethyl)-3-methoxyphenyl)tetrazole
5-(2-(4-(2-quinolinylmethyloxy)phenoxymethyl)-3-methylphenyl)tetrazole
5-(3-(4-(2-quinolinylmethyloxy)phenoxymethyl)-4-methoxyphenyl)tetrazole
5-(3-(3-(2-quinolinylmethyloxy)phenoxymethyl)-4-methoxyphenyl)tetrazole
5-(4-(3-(2-quinolinylmethyloxy)-5-methylphenoxymethyl)-2-methoxyphenyl)tetrazole
5-(4-(3-(2-quinolinylmethyloxy)-N-acetylphenylaminomethyl)phenyl)tetrazole
5-(4-(3-(2-quinolinylmethylthio)-N-acetylphenylaminomethyl)phenyl)tetrazole

EXAMPLE 32

5-(3-(4-(2-Quinolinylmethyloxy)Phenoxymethyl)-Phenoxymethyl)Tetrazole

A. α-(3-hydroxymethylphenoxy)acetonitrile

A mixture of 3-hydroxymethyl phenol (0.081 mol), bromacetonitrile (0.081 mol) and anhydrous potassium carbonate (0.081 mol) in acetone (160 ml) and dimethylformamide (20 ml) are heated at reflux for 48 hrs. The reaction mixture is filtered and evaporated. The residue is diluted with ethyl acetate (150 ml), washed with 10% aqueous sodium hydroxide solution (3×100 ml) and then with brine (3×100 ml). The ethyl acetate solution is dried (magnesium sulfate) and chromatographed using a silica gel column (ca. 100 g) and eluted with 1:1 petroleum ether: ethylacetate (2l). The resultant oil is used directly in the next step.

B. α-(3-chloromethylphenoxy)acetonitrile

α-(3-Hydroxymethylphenoxy)acetonitrile (0.055 mol) in diethylether (150 ml) is stirred with thionyl chloride (0.060 mol) and a few drops of dimethylformamide at 40° C. for 1 hr. the solution is washed with water and brine, then evaporated to give α-(3-chloromethylphenoxy)acetonitrile as a yellow oil which is used directly in the next step.

C. α-(3-(4-(2-quinolinylmethyloxy)phenoxymethyl)-phenoxy) acetonitrile

A mixture of α-(3-chloromethylphenoxy)acetonitrile (0.025 mol), sodium 4-(2-quinolinylmethyloxy)phenoxide (0.025 mol and anhydrous potassium carbonate (0.125 mol) in dimethylsulfoxide (50 ml) is stirred at ambient temperature for 18 hrs. The reaction is diluted with water (600 ml) and extracted with ethyl acetate (3×150 ml). The ethyl acetate solution is washed with water (3×100 ml) and brine (100 ml) then dried and evaporated to give α-(3-(4-(2-quinolinylmethyloxy)-phenoxymethyl)phenoxy)acetonitrile. (M.P. 110°-114° C.)

D. 5-(3-(4-(2-quinolinylmethyloxy)phenoxymethyl)-phenoxymethyl)tetrazole

α-(3-(4-(2-quinolinylmethyloxy)phenoxymethyl)-phenoxy)acetonitrile (8.12 mmol), sodium azide (24.4 mmol) and ammonium chloride (24.4 mmol) in dimethylformamide (10 ml) are heated at 115°-120° C. for 6 hrs. After cooling, the reaction mixture is diluted with ethyl acetate (150 ml), washed with water (6×100 ml) then dried and evaporated. The residue is chromatographed on a column of silica gel (360 g) and eluted with a gradient of isopropanol in methylene chloride to give 5-(3-(4-(2-quinolinylmethyloxy)phenoxymethyl)-phenoxymethyl)tetrazole (M.P. 131°–132° C.)

EXAMPLE 33

When sodium 4-(2-quinolinylmethyloxy)phenoxide of Example 32, Step C, is replaced with sodium 3-(2-quinolinylmethyloxy)phenoxide, the product prepared is 5-(3-(3-(2-quinolinylmethyloxy)phenoxymethyl)-phenoxymethyl)tetrazole. (M.P. 135°–137° C.)

EXAMPLE 34

When α(3-hydroxymethylphenoxy)acetonitrile of Example 33, Step B, is replaced with α(4-hydroxymethylphenoxy)acetonitrile then the produce prepared is 5-(4-(3-(2-quinolinylmethyloxy)phenoxymethyl)-phenoxymethyl)tetrazole. (M.P. 154°–156° C.)

EXAMPLE 35

When α(3-hydroxymethylphenoxy)acetonitrile of Example 33, Step B, is replaced with α(2-hydroxymethylphenoxy)acetonitrile or α[(2-hydroxymethyl-5-carbomethoxy)phenoxy)acetonitrile then the products prepared are 5-(2-(3-(2-quinolinylmethyloxy)phenoxymethyl)phenoxymethyl)tetrazole (M.P. 118°–120° C.) or 5-(2-(3-(2-quinolinylmethyloxy)phenoxymethyl)-5-carbomethoxy-phenoxymethyl)tetrazole. (M.P. 159°–162° C.)

EXAMPLE 36

When bromoacetonitrile of Example 32, Step A is replaced by the nitriles of Table XIII below then the corresponding product is prepared:

TABLE XII bromoacetonitrile
α-bromo-α-methylacetonitrile
α-bromo-β-ethylacetonitrile
α-bromopropionitrile
β-bromopropionitrile
β-bromo-β-methylpropionitrile -bromobutyronitrile
β-bromobutyronitrile
α-bromobutyronitrile

EXAMPLE 37

When 3-hydroxymethylphenol of Example 32, Step A is replaced by the compounds of Table XIII below, then the corresponding products are prepared.

TABLE XIII 2-hydroxymethylphenol
3-hydroxymethylphenol
4-hydroxymethylphenol
3-mercaptobenzylalcohol
4-mercaptobenzylalcohol
3-hydroxymethyl-N-acetylamidine
4-hydroxymethyl-N-acetylamidine
4-hydroxymethylamidine
4-methyl-2-hydroxymethylphenol
2-methyl-5-hydroxymethylphenol
4-methyl-3-hydroxymethylphenol
5-methyl-3-hydroxymethylphenol
3-methyl-4-hydroxymethylphenol
2-methyl-4-hydroxymethylphenol
3-methyl-5-hydroxymethylphenol
4-methoxy-3-hydroxymethylphenol
3-methoxy-4-hydroxymethylphenol
2-methoxy-4-hydroxymethylphenol
5-methoxy-3-hydroxymethylphenol
3-methoxy-5-hydroxymethylphenol
2-methoxy-5-hydroxymethylphenol
2-(1'-hydroxyethyl)phenol
3-(1'-hydroxyethyl)phenol
4-(1'-hydroxyethyl)phenol
2-(2'-hydroxyethyl)phenol
3-(2'-hydroxyethyl)phenol
4-(2'-hydroxyethyl)phenol
2-(3'-hydroxypropyl)phenol
3-(3'-hydroxypropyl)phenol
4-(3'-hydroxypropyl)phenol
2-(2'-hydroxypropyl)phenol
3-(2'-hydroxypropyl)phenol
4-(2'-hydroxypropyl)phenol
2-(1'-hydroxypropyl)phenol
3-(1'-hydroxypropyl)phenol
4-(1'-hydroxypropyl)phenol
3-(4'-hydroxybutyl)phenol
4-(4'-hydroxybutyl)phenol

EXAMPLE 38

Following the procedures of Examples 32 to 34, when sodium 4-(2-quinolinylmethyloxy)phenoxide of Example 32, Step C, is replaced by the metal hydroxy, thio or amino salts of the compounds of Table VIII, Example 24, then the corresponding product is prepared. Representative examples of compounds prepared by this invention are shown in Table XIII.

TABLE XIII 5-(4-(4-(2-quinolinylmethyloxy)phenoxymethyl)-phenoxymethyl)tetrazole
5-(4-(2-(2-quinolinylmethyloxy)phenoxymethyl)-phenoxymethyl)tetrazole
5-(3-(2-(2-quinolinylmethyloxy)phenoxymethyl)-phenoxymethyl)tetrazole
5-(2-(4-(2-quinolinylmethyloxy)phenoxymethyl)-phenoxymethyl)tetrazole
5-(2-(3-(2-quinolinylmethyloxy)phenoxymethyl)-phenoxymethyl)tetrazole
5-(2-(2-(2-quinolinylmethyloxy)phenoxymethyl)-phenoxymethyl)tetrazole
5-(3-(4-(2-quinolinylmethyloxy)phenoxymethyl)-2-methoxyphenoxymethyl)tetrazole
5-(3-(4-(2-quinolinylmethyloxy)phenoxymethyl)-3-methoxyphenoxymethyl)tetrazole
5-(4-(3-(2-quinolinylmethyloxy)phenoxymethyl)-2-methoxyphenoxymethyl)tetrazole
5-(4-(3-(2-quinolinylmethyloxy)phenoxymethyl)-3-methoxyphenoxymethyl)tetrazole
5-(4-(3-(2-quinolinylmethyloxy)phenoxymethyl)-3-methylphenoxymethyl)tetrazole
5-(4-(4-(2-quinolinylmethyloxy)phenoxymethyl)-2-methoxyphenoxymethyl)tetrazole
5-(4-(4-(2-quinolinylmethyloxy)phenoxymethyl)-3-methoxyphenoxymethyl)tetrazole
5-(4-(4-(2-quinolinylmethyloxy)phenoxymethyl)-3-methylphenoxymethyl)tetrazole
5-(4-(4-(2-quinolinylmethyloxy)phenoxymethyl)-2-methylphenoxymethyl)tetrazole
5-(4-(4-(2-quinolinylmethyloxy)-2-methylphenoxymethyl)phenoxymethyl)tetrazole
5-(4-(4-(2-quinolinylmethyloxy)-3-methylphenoxymethyl)phenoxymethyl)tetrazole
5-(4-(4-(2-quinolinylmethyloxy)-3-methoxyphenoxymethyl)phenoxymethyl)tetrazole
5-(3-(3-(2-quinolinylmethyloxy)-4-methoxyphenoxymethyl)phenoxymethyl)tetrazole 5-(3-(3-(2-quinolinylmethyloxy)-4-methoxyphenoxymethyl)phenoxymethyl)tetrazole
5-(4-(4-(2-quinolinylmethyloxy)-2-methylphenoxymethyl)-3-methylphenoxymethyl)tetrazole
5-(4-(4-(2-quinolinylmethyloxy)-3-methylphenoxymethyl)-2-methylphenoxymethyl)tetrazole
5-(2-(3-(4-(2-quinolinylmethyloxy)-phenoxymethyl)phenoxy)ethyl)tetrazole
5-(3-(3-(4-(2-quinolinylmethyloxy)-phenoxymethyl)phenoxy)propyl)tetrazole
5-(2-(3-(4-(2-quinolinylmethyloxy)-phenoxymethyl)phenoxy)propyl)tetrazole
5-(3-(3-(4-(2-quinolinylmethyloxy)-phenoxymethyl)phenoxy)butyl)tetrazole
5-(4-(4-(2-quinolinylmethyloxy)-phenythiomethyl)phenoxymethyl)tetrazole
5-(4-(4-(2-quinolinylmethyloxy)-phenythiomethyl)phenylthiomethyl)tetrazole
5-(4-(4-(2-quinolinylmethylthio)-phenoxymethyl)phenoxymethyl)tetrazole
5-(4-(4-(2-quinolinylmethyloxy)-phenoxymethyl)phenyl-N-acetylaminomethyl)tetrazole
5-(3-(4-(4-(2-quinolinylmethyloxy)-phenoxymethyl)phenylthio)butyl)tetrazole
5-(3-(3-(4-(2-quinolinylmethyloxy)phenoxy-1'-ethyl)phenoxymethyl)tetrazole
5-(3-(3-(4-(2-quinolinylmethyloxy)phenoxy-2'-propyl)phenoxymethyl)tetrazole
5-(3-(3-(4-(2-quinolinylmethyloxy)phenoxy-3'-butyl)phenoxymethyl)tetrazole

EXAMPLE 39

3-(3-(2-Quinolinylmethyloxy)Benzyloxy)Benzaldehyde

When 3-hydroxybenzonitrile in Example 7 is replaced by 3-hydroxybenzaldehyde then the product prepared is 3-[3-(2-quinolinylmethyloxy)benzyloxy)benzaldehyde.

EXAMPLE 40

When 3-hydroxybenzaldehyde of Example 39 is replaced by the compounds of Table XIV below, then the corresponding product is obtained.

TABLE XIV 2-hydroxybenzaldehyde
3-hydroxybenzaldehyde
4-hydroxybenzaldehyde
2-methyl-3-hydroxybenzaldehyde
5-methyl-3-hydroxybenzaldehyde
2-methyl-4-hydroxybenzaldehyde
3-methyl-4-hydroxybenzaldehyde
5-methoxy-3-hydroxybenzaldehyde
4-methoxy-3-hydroxybenzaldehyde
2-methoxy-3-hydroxybenzaldehyde
5-carbomethoxy-3-hydroxybenzaldehyde
3-hydroxyphenylacetaldehyde
4-hydroxyphenylacetaldehyde
3-hydroxyphenylpropionaldehyde
4-hydroxyphenylpropionaldehyde
3-hydroxyphenylisopropionaldehyde
4-hydroxyphenylisopropionaldehyde
3-hydroxyphenoxyacetaldehyde
4-hydroxyphenylthiopropionaldehyde

EXAMPLE 41

When 3-2-quinolinylmethyloxy)benzyl chloride of Example 39 is replaced by the compounds prepared by Examples 2-6 and 3-hydroxybenzaldehyde of Example 39 is replaced by the compounds of Table XIV, Example 40, then the corresponding products are obtained.

EXAMPLE 42

3-(3-(2-Quinolinylmethyloxy)Benzyloxy)Cinnamylnitrile

Sodium hydride (60% oil dispersion, 1.2 g) and diethyl cyanomethylphosphonate (5 ml) are combined and stirred in THF (50 ml) for 5 minutes. This is then added to a THF solution of 3-(3-(2-quinolinylmethyloxy)benzyloxy)benzaldehyde (9.59 g). The reaction mixture is stirred for an additional 30 minutes and poured into ice water. The crude product is filtered and chromatographed through a silica gel dry column using chloroform as the eluant to give 3-(3-(2-quinolinylmethyloxy)benzyloxy)cinnamylnitrile.

EXAMPLE 43

When 3-(3-(2-quinolinylmethyloxy)benzyloxy)benzaldehyde of Example 42 is replaced by the compounds of Example 41, the corresponding product is prepared.

When diethylcyanomethylphosphonate in the above Example is replaced by diethylcyanoethylphosphate, diethylcyanopropylphospate or diethylcyanoisopropylphosphate then the corresponding products are obtained.

EXAMPLE 44

5-(3-(3-(2-Quinolinylmethyloxy)Benzyloxy)Styryltetrazole Hydrochloride

A mixture of 3-(3-(2-quinolinylmethyloxy)benzyloxy)cinnamylnitrile (0.03 mol), anhydrous aluminum chloride (0.03 mol) and sodium azide (0.09 mol) in THF (30 ml) is stirred and refluxed for 18 hours. Hydrochloric acid (18% HCl 15 ml) is added and thereafter the reaction mixture is poured into ice water. The precipitate is collected and then recrystallized from methanol-ethyl acetate to obtain pure 5-(3-(3-(2-quinolinylmethyloxy)benzyloxy)styryl)tetrazole hydrochloride.

The free base is obtained by treatment of the salt with one equivalent of sodium hydroxide solution followed by removal of sodium chloride and water.

EXAMPLE 45

When (3-(3-(2-quinolinylmethyloxy)benzyloxy)cinnamylnitrile of Example 44 is replaced by the compounds formed in Example 43, then the corresponding product is prepared. Representative compounds prepared by this invention are described in Table XV.

TABLE XV 5-(4-(3-(2-quinolinylmethyloxy)phenoxy)styryl)tetrazole
5-(4-(3-(2-quinolinylmethyloxy)benzyloxy)styryl)tetrazole
5-(3-(4-(2-quinolinylmethyloxy)benzyloxy)styryl)tetrazole
5-(4-(4-(2-quinolinylmethyloxy)benzyloxy)styryl)tetrazole
5-(4-(3-(2-quinolinylmethyloxy)-4-methylbenzyloxy)styryl)tetrazole
5-(4-(3-(2-quinolinylmethyloxy)benzyloxy)3-methylstyryl)tetrazole
5-(3-(3-(2-quinolinylmethylthio)benzyloxy)styryl)tetrazole
5-(3-(4-(2-quinolinylmethylthio)phenoxy)styryl)tetrazole 5-(3-(4-(2-quinolinylmethyloxy)benzylthio)styryl)tetrazole 5-(3-(4-(3-(2-quinolinylmethyloxy)benzyloxy)phenoxy)2-propen-1-yl)tetrazole

EXAMPLE 46

3-Methylcarboethoxy-5-(4-(3-(2-Quinolinylmethyloxy)-Phenoxymethyl)Phenyl)Tetrazole To a solution of 0.2 g sodium in 30 ml ethanol is first added 1 g of 5-(4-(3-(2-quinolinylmethyloxy)phenoxymethyl)phenyl)tetrazole and then after 30 minutes 0.6 g of ethylbromoacetate and stirring is continued at 80° C. for 16 hours. The solvent is then removed, diluted with water, filtered, washed with ether and dried to give the desired compound, also referred to as ethyl 5-(4-(3-(2-quinolinylmethyloxy)phenoxymethyl)-phenyl)tetrazole-3-yl acetate.

When ethylbromoacetate in the above procedure is replaced with N,N-diethyl-α-bromoacetamide, N,N-diethyl-aminoethyl bromide or N-acetylaminoethyl bromide or N-acetyl-α-bromoacetamide, then the corresponding products are obtained.

EXAMPLE 47

5-(4-(3-(2-Quinolinylmethyloxy)Phenoxymethyl)-Phenyl)Tetrazol-3-Yl) Acetic Acid

A mixture of 1 g of ethyl [5-(4-(3-(2-quinolinylmethyloxy)phenoxymethyl)phenyl)tetrazol-3-yl] acetate in 5 ml ethanol and 40 ml of 1N NaOH is stirred at 70° C. for 4 hours. This is cooled, diluted with water, acidified with acetic acid, filtered, washed with water, and then ethyl acetate to give 5-(4-(3-(2-quinolinylmethyloxy)-phenoxymethyl)phenyl)tetrazol-3-yl acetic acid.

In a similar manner, the substituted tetrazoles of this invention may be prepared.

EXAMPLE 48

4-(4-(2-Quinolinylmethylsulfonyl)Phenoxymethyl)Benzoic Acid

A. 4-(4-(2-quinolinylmethylthio)phenoxymethyl)benzoic acid (4 mmol) in dichloroethene (50 ml) is stirred with m-chloroperbenzoic acid (4 mmol) and solid potassium hydrogen carbonate (1.0 g). The reaction is assayed by TLC and upon consumption of the starting thio compound, the mixture is filtered, washed with dilute aqueous sodium bisulfite, dried and evaporated to give 4-(4-(2-quinolinylmethylsulfinyl)phenoxymethyl)-benzoic acid.

B. To 3 mmol of the sulfinyl compound from Step A in acetic acid (40 mmol) is added 30% hydrogen peroxide (2 ml). The mixture is stirred at ambient temperature and assayed by TLC. Upon disappearance of the sulfinyl starting compound, the reaction mixture is diluted with dichloromethane, washed with dilute aqueous sodium bisulfite and water, dried and evaporated to give 4-(4-(2-quinolinylmethylsulfonyl)phenoxymethyl)-benzoic acid.

In a similar manner, the sulfinyl and sulfonyl compounds of this invention may be prepared.

EXAMPLE 49

5-(3-Methyl-4-(4-(4-(2-Quinolinylmethyloxy)Benzyloxy)Phenyl)Butyl)Tetrazole

A. 4-benzyloxy-α-methyl-cinnamic acid ethyl ester. To a solution of sodium hydride (60% oil dispersion, 3.1 g) and diethyl 2-phosphonopropionate (15.5 g) in tetrahydrofuran (50 ml) is added dropwise a tetrahydrofuran solution of 4-benzyloxy-benzaldehyde (10.6 g). After stirring at room temperature for 2 hours, the reaction mixture is poured into ice water. The insoluble solid is collected, and used directly in the next step.

B. 4-benzyloxy-α-methyl-cinnamic alcohol. Under argon and with stirring, a tetrahydrofuran solution of 4-benzyloxy-α-methyl-cinnamic acid ethyl ester (11.9 g) is added dropwise to a cooled tetrahydrofuran solution of lithium aluminum hydride (2.5 g). The reaction mixture is allowed to stir for 18 hours and afterward, the excess reagent is destroyed in a conventional manner. The residue which results from the evaporation of the solvent is partitioned in a water/ethyl acetate mixture and from the organic layer, the desired product is obtained. This is used directly in the next step.

C. 4-benzyloxy-α-methyl-cinnamyl aldehyde. Manganese dioxide (15 g total) is added portionwise to a dichloromethane solution (100 ml) of 4-benzyloxymethylcinnamic alcohol with stirring over a period of one week. After two filtrations, the filtrate is evaporated to yield a gum. Upon treatment with cold hexane, the crude product results which is used directly in the next step.

D. 5-(p-benzyloxyphenyl)-4-methyl-2,4-pentadienenitrile. To a solution of sodium hydride (60% oil dispersion, 1.5 g) and diethyl cyanomethylphosphonate (5.4 g) in tetrahydrofuran (50 ml) is added dropwise a tetrahydrofuran solution of 4-benzyloxy-α-methyl-cinnamyl aldehyde (4.8 g). After stirring at room temperature for 2 hours, the reaction mixture is poured into ice water. The insoluble material is collected and used directly in the next step.

E. 5-(p-hydroxyphenyl-4-methylvaleronitrile. 5-(p-Benzyloxyphenyl)-4-methyl-2,4-pentadienenitrile (4.3 g) dissolved in ethanol is hydrogenated (0.8 g of 5% palladium over charcoal as catalyst) around 30 psi overnight. After filtering off the catalyst, the solvent is evaporated to give an oil which is used directly in the next step.

F. 4-methyl-5-(4-(4-(2-quinolinyloxymethyl)benzyloxy)phenyl)valeronitrile. A reaction mixture of 5-p-hydroxyphenyl-4-methyl-valeronitrile (2.9 g), 4-(2-quinolinylmethyloxy)benzyl chloride hydrochloride (6.3 g) and anhydrous potassium carbonate (30 g) in dimethylformamide (60 ml) is stirred and heated (110° C.) for 5 hours. Afterward, the solvent is removed under vacuum and the residue is partitioned in a mixture of chloroform/water. The organic layer is evaporated and the resultant oil is purified on a silica gel dry column (chloroform as eluant) to give product which may used directly in the next step.

G. 5-(3-methyl-4-(4-(4-(2-quinolinylmethyloxy)-phenyl)butyl)tetrazole. A mixture of 4-methyl-5-(4-(4-(2-quinolinylmethyloxy)benzyloxy)phenyl) valeronitrile (1.5 g.), sodium aside (3 g), ammonium chloride (1.9 g) in dimethylformamide (20 ml) is stirred and heated at 135° C. for 18 hours. After cooling, the reaction mixture is poured into ice water and the insoluble material is taken up by chloroform. The residue from the evaporation of chloroform is purified by silica gel dry column (5% methanol in chloroform as eluant) to yield 5-(3-methyl-4-(4-(4-(2-quinolinylmethyloxy)benzyloxy)-phenyl)butyl)tetrazole.

EXAMPLE 50

When 2-chlormethylquinoline of Example 49, Part F is replaced by the quinoline compounds of Examples 5 and 6, then the corresponding product is obtained. When the products are treated according to the procedures of Steps F and G, then the corresponding tetrazole products are obtained.

EXAMPLE 51

When diethyl 2-phosponopropionate of Example 49, Step A is replaced by the Wittig reagents of Table XVI below then the corresponding products are obtained.

TABLE XVI diethyl 2-phosphonoacetate
diethyl 2-phosphonopriopionate
diethyl 3-phosphonopropionate
diethyl 4-phosphonobutyrate
diethyl 3-phosphonobutyrate
diethyl 2-phosphonobutyrate
diethyl 5-phosphonopentanoate
diethyl 4-phosphonopentanoate
diethyl 3-phosphonopentanoate
diethyl 4-phosphono-3-methylbutyrate
diethyl 4-phosphono-2,3-dimethylbutyrate
diethyl 5-phosphono-4-methylpentanoate
diethyl 5-phosphono-3,4-dimethylpentanoate
diethyl 4-phosphono-3,3-dimethylbutyrate
diethyl 4-phosphono-3-phenylbutyrate
diethyl 4-phosphono-3-benzylbutyrate
diethyl 3-phosphono-2,2-dimethylpropionate
diethyl 4-phosphono-2-propylbutyrate
diethyl 4-phosphono-3-propylbutyrate
diethyl 3-phosphonomethylhexanoate
diethyl 4-phosphonoheptanoate

EXAMPLE 52

When diethylcyanomethylphosphonate of Example 49, Step D is replaced by the Wittig reagents of Table XVII below then the corresponding products are obtained.

TABLE XVII diethyl 2-phosphonoacetonitrile
diethyl 3-phosphonopropionitrile
diethyl 2-phosphonopropionitrile
diethyl 4-phosphonobutyronitrile
diethyl 3-phosphonobutyronitrile
diethyl 2-phosphonobutyronitrile
diethyl 5-phosphonopentanonitrile
diethyl 4-phosphonopentanonitrile
diethyl 3-phosphonopentanonitrile
diethyl 2-phosphonopentanonitrile
diethyl 4-phosphono-5-phenylpentanonitrile
diethyl 4-phosphono-3-phenylbutyronitrile
diethyl 4-phosphono-5-cyclopropylpentanonitrile
diethyl 4-phosphonohexanonitrile
diethyl 4-phosphonoheptanonitrile
diethyl 4-phosphono-5-carbethoxypentanonitrile
diethyl 4-phosphono-3-methylenebutyronitrile
diethyl 4-phosphono-3-ethylidenebutyronitrile
diethyl 1-phosphonomethyl-1-cyanoethylcyclopropane
diethyl 1-phosphonomethyl-1-cyanomethylcyclobutane
diethyl 1-phosphonomethyl-2-cyanomethylcyclobutane
diethyl 1-phosphonomethyl-2-cyanomethylcyclopentane

EXAMPLE 53

When diethyl 2-phosphonopropionate of Example 49, Step A is replaced by the Wittig reagents of Table XVII, Example 52, then the corresponding products are obtained. When these products are then treated according to the procedure of Example 50, then the corresponding product is obtained.

EXAMPLE 54

When 4-hydroxy-3-methoxybenzoate of Example 14 is replaced with 3-hydroxymethylphenol, then the product prepared is 3-(3-(2-quinolinylmethyloxy)benzyloxy)benzyl alcohol.

EXAMPLE 55

When 4-hydroxy-3-methoxybenzoate of Example 14 is replaced with the compounds of Table XVIII below and 3-(2-quinolinylmethyloxy)benzyl chloride is replaced by the compounds of Example 6, then the corresponding products are prepared.

TABLE XVIII 1,2-dihydroxybenzene
1,3-dihydroxybenzene
1,4-dihydroxybenzene
2-mercaptophenol
3-mercaptophenol
4-mercaptophenol
1,3-dimercaptobenzene
3-hydroxymethylphenol
3-hydroxyethylphenol
3-mercaptomethylphenol
4-hydroxymethylphenol
4-hydroxyethylphenol
2-methylresorsinol
5-methylresorsinol
5-methyl-1,4-dihydroxybenzene

EXAMPLE 56

5-(3-Chloropropyl)Tetrazole

A mixture of 3.5 g of 4-chlorobutyronitrile, 2.3 g of sodium azide and 1.9 g of ammonium chloride in 50 ml of dimethyl-formamide is stirred at 140° C. for 20 hours. The reaction mixture is poured onto ice, basified with 1N sodium hydroxide and extracted twice with ethyl acetate. The aqueous fraction is acidified with acetic acid and extracted with ethylacetate. Evaporation of the ethyl acetate gives 5-(3-chloropropyl)-tetrazole which is used directly in the next step.

EXAMPLE 57

When 4-chlorobutyronitrile of Example 56 above is replaced by the nitriles of Table XIX below then the corresponding tetrazole product is obtained.

TABLE XIX chloracetonitrile
bromoacetonitrile
3-chloropropionitrile
4-chlorobutyronitrile
5-chloropentanonitrile
6-chlorohexanonitrile
2-chloropropionitrile
2-methyl-3-chloropropionitrile
2-chlorobutyronitrile
3-chlorobutyronitrile
4-methyl-5-chloropentanonitrile
2-methyl-3-chloropropinonitrile
3-benzyl-4-chlorobutyronitrile
3-carbethoxymethyl-4-chlorobutyronitrile
3-methoxymethyl-4-chlorobutyronitrile 2,3-dimethyl-4-chloropentanonitrile
3,3-dimethyl-4-chloropentanonitrile
spiro-(3,3-cyclopropane)4-chlorobutyronitrile
1-chloromethyl-2-cyanomethylcyclobutane
1-chloromethyl-2-cyanomethylcyclohexane
3-cyclopropylmethyl-4-chlorobutyronitrile
3-dimethylaminomethyl-4-chlorobutyronitrile
3-methylene-4-chlorobutyronitrile
3-propylidene-4-chlorobutyronitrile

EXAMPLE 58

5-(4-(3-(3-(2-Quinolinylmethyloxy)Benzyloxy)Phenyl)-Butyl)Tetrazole

A mixture of (0.014 mol) 3-(3-(2-quinolinylmethyloxy)benzyloxy)benzyl alcohol (0.14 mol) 5-(3-chloropropyl)tetrazole and 2 g (0.036 mol KOH in 5 ml water and 50 ml ethanol is heated over a steam bath for a period of 3 hours. Reaction mixture is concentrated to dryness and slurried into water and extracted with methylene chloride. The methylene chloride extract is washed with water, dried over MgSO4 and concentrated under reduced pressure to obtain solid which is passed through a silica gel column using hexane/ethyl acetate as eluent. Evaporation of eluent gives 5-(4-(3-(3-(2-quinolinylmethyloxy)benzyloxy)phenyl)butyl)tetrazole.

EXAMPLE 59

When 3-(3-(2-quinolinylmethyloxy)benzyloxy)benzyl alcohol of Example 58 is replaced by the compounds prepared by Examples 54 and 55 and 5-(3-chloropropyl)tetrazole is replaced by the compounds prepared by Example 57, then the corresponding product is obtained.

TABLE XX 5-(4-(4-(3-(2-quinolinylmethyloxy)benzyloxy)phenyl)-butyl)tetrazole
5-(3-(4-(3-(2-quinolinylmethyloxy)benzyloxy)phenyl)-butyl)tetrazole
5-(3-(4-(4-(2-quinolinylmethyloxy)benzyloxy)phenyl)-butyl)tetrazole
5-(2-(3-(3-(2-quinolinylmethyloxy)benzyloxy)phenyl)-propyl)tetrazole
5-(3-(3-(3-(2-quinolinylmethylthio)benzyloxy)phenyl)-butyl)tetrazole
5-(3-(3-(3-(2-quinolinylmethyloxy)benzyloxy)phenyl)-butyl)tetrazole
5-(3-(3-(3-(2-quinolinylmethyloxy)benzylthio)phenyl)-butyl)tetrazole
5-(4-(3-(3-(2-quinolinylmethyloxy)benzyloxy)phenyl)-butyl)tetrazole
5-(3-(3-(3-(2-quinolinylmethyloxy)phenoxy)phenyl)-butyl)tetrazole

EXAMPLE 60

When 3-hydroxybenzonitrile in Example 7 is replaced by 3-hydroxybenzaldehyde then the product prepared is 3-(2-quinolinylmethyloxy)benzaldehyde.

EXAMPLE 61

When 3-hydroxybenzaldehyde in Example 60 is replaced by the compounds of Table XIV, Example 40 and 3-(2-quinolinylmethyloxy)benzyl chloride is replaced by the chlorides prepared in Examples 5 and 6, then the corresponding product is prepared.

EXAMPLE 62

5-(4-(3-(2-Quinolinylmethyloxy)Benzoylmethyl)-Phenyl)Tetrazole

A. 2-(3-(2-quinolinylmethyloxy)phenyl)-1,3-dithiane. A 1M solution of 3-(2-quinolinylmethyloxy)benzaldehyde (0.01 mol) in chloroform is combined with an equimolar amount of 1,3 propane-dithiol at −20° C. Dry HCl gas is slowly passed through the solution for 5–10 minutes. The reaction mixture is then allowed to come to room temperature. After 3 hours, the reaction mixture is worked up by successively washing with water, 10% aqueous KOH and water and drying over K2CO3. Evaporation of the solvent furnishes the desired product which is purified by column chromatography to give product which is used directly in the next step.

B. 2-(3-(2-quinolinylmethyloxy)phenyl-2-(p-cyanobenzyl)-1,3-dithiane. To a 0.2M THF solution of the 2-(3-(2-quinolinyl-methyloxy)phenyl)-1,3-dithiane (0.01 mol) under N2 is added a 5% excess of N-butyl lithium in N -hexane (2.5M) at a rate if 3–5 ml/min at −78° C. After 3 hours, 4-cyanobenzylchloride (0.01 mol in 20 ml of THF) is added dropwise over a period of 10 minutes. Let stir 3 hours at −78° C. and then allow the reaction mixture to come to 0° C. slowly. The mixture is poured into 3 volumes of water, extracted with chloroform furnishing an organic solution which is washed twice with water, 7% aqueous KOH and again with water. The organic layer is dried over K2CO3 and is concentrated. The crude product is purified by column chromatography to give the desired product which is used directly in the next step.

C. 4-(3-(2-quinolinylmethyloxy)benzoylmethyl)benzonitrile. To a solution of 2-(3-(2-quinolinylmethyloxy-1,3-dithiane (1.0 mmol) in 80% aqueous acetonitrile (10 ml) is added mercuric chloride (2.2 mmol) as a solution in the same solvent mixture. Mercuric oxide (1.1 mmol) is then added to buffer the reaction mixture near pH=7. The dithianemercuric chloride complex separates as a white precipitate. The reaction mixture is refluxed under nitrogen for 5 hours, then cooled and filtered through Super Gel. The filter cake is washed thoroughly with 1:1 hexane-dichloromethane. The organic phase is washed with 5M aqueous ammonium acetate. water and brine. The organic phase is then dried with MgSO4, and is concentrated to give the crude product which is purified by column chromatography to give 4-(3-(2-quinolinylmethyloxy)benzoylmethyl)benzonitrile.

D. 5-(4-(3-(2-quinolinylmethyloxy)benzoylmethyl)-phenyl)tetrazole. A heterogenous mixture of 4-(3-(2-quinolinylmethyloxy)benzoylmethyl)benzonitrile (1.35 mmol). NaN3 (6.77 mmol), pyridinium hydrochloride (6.77 mmol) in DMF (3 ml) is heated at 100° C. for 3 hours under nitrogen. The reaction mixture is poured into water and the product is collected on a filter. Recrystallization from EtOAc - DMF gives 5-(4-(3-(2-quinolinylmethyloxy)benzoylmethyl)phenyl)tetrazole.

EXAMPLE 63

When 3-(2-quinolinylmethyloxy)benzaldehyde in Example 62, Step A is replaced by the aldehydes of Example 61, and 4-cyanobenzyl chloride of Example 62, Step B is replaced by the compounds of Table X, Example 29 or Table VII, Example 23, then the corresponding products are obtained. Representative compounds prepared by this invention are shown in Table XXI.

TABLE XXI 5-(4-(4-(2-quinolinylmethyloxy)benzoylmethyl)-phenyl)tetrazole 5-(4-(3-(2-quinolinylmethyloxy)benzoylmethyl)benzyl)-tetrazole 5-(3-(4-(3-(2-quinolinylmethyloxy)benzoylmethyl)-phenyl)propyl)tetrazole 5-(3-(3-(2-quinolinylmethylthio)benzoylmethyl)-phenyl)tetrazole 5-(4-(3-(2-quinolinylmethyloxy)benzoylethyl)benzyl)-tetrazole

EXAMPLE 64

5-(3-(3-(2-Quinolinylmethyloxy)Benzoylamino)-Phenyl)Tetrazole

A. 3-(2-quinolinylmethyloxy)benzoic acid. A mixture of 28.16 g (0.132 mol) of 2-quinolinylmethyl chloride HCl, 18 g (0.132 mol) of 3-hydroxybenzoic acid and 39.6 g of potassium carbonate in 110 ml of DMF is heated at 70° C. overnight. The reaction mixture is poured into water, and the precipitated product is collected, filtered and dried to give 3-(2-quinolinylmethyloxy)benzoic acid.

B. 3-(2-quinolinylmethyloxy)benzoic acid chloride. A mixture of 15.6 g (0.1 mol) of 3-(2-quinolinylmethyloxy)benzoic acid and 11.9 g (0.1 mol) of thionyl chloride is refluxed for 4 hours. The reaction mixture is then evaporated to dryness at room temperature and used directly in the next step.

C. 3-(3-(2-quinolinylmethyloxy)benzoylamino)benzonitrile. A solution of 3-aminobenzonitrile (10 mmol) in 50 ml of chloroform and triethylamine (11 mmol) is added to a solution of 10 mmol of 3-(2-quinolinylmethyloxy)benzoic acid chloride in 20 ml of chloroform over a period of 10 minutes. The reaction is stirred at room temperature for 2 hours and is poured into water and then extracted into chloroform. The organic solution is dried and evaporated to give 3-(3-(2-quinolinylmethyloxy)benzoylamino)-benzonitrile.

D. 5-3-(3-(2-quinolinylmethyloxy)benzoylamino)-phenyl)tetrazole. A mixture of 10 mmol of 3-(3-(2-quinolinylmethyloxy)benzoylamino)benzonitrile, 50 mmol of sodium azide, and 50 mmol of pyridine HCl in 30 ml of DMF is heated at 100° C. for 2 days. The reaction mixture is poured into water, and the product is collected on a filter. Recrystallization from ethyl acetate and DMF gives 5-3-(3-(2-quinolinylmethyloxy)-benzoylamino)phenyl)tetrazole.

In a similar manner, the compounds of this invention where B is

may be made.

EXAMPLE 65

5-3-(3-(2-Quinolinylmethyloxy)Anilinocarbonyl)-Phenyl)Tetrazole

When the procedure of Example 64 is followed and 3-(2-quinolinylmethyloxy)aniline is used in place of 3-aminobenzonitrile and 3-cyanobenzoic acid is used in place of 3-(2-quinolinylmethyloxy) benzoic acid, then the product prepared is 5-3-(3-(2-quinolinylmethyloxy)anilinocarbonyl)phenyl)tetrazole.

In a similar manner, the compounds of this invention where B is

may be made.

The methods described above are used to prepare the following compounds of this invention.

5-[2-(4-(2-Quinolinylmethyloxy)phenoxymethyl)benzyl]tetrazole (M.P.) 108°–111° C.) CALC: C, 59.87; H, 5.96; N, 13.96; FOUND: C, 59.67, 60.01; H, 5.62, 5.63; N, 13,73, 13.77.

5-[4-Methoxy-3-(3-(2-quinolinylmethyloxy)phenoxymethyl)phenyl]tetrazole (M.P. 184°–87° C.)

CALC: C, 67.63; H, 4.88; N, 15.78; FOUND: C, 67.18; H, 5.13; N, 15.40.

5-[3-(4-(2-quinolinylmethyloxy)phenoxymethyl)-phenyl]tetrazole (M.P. 176°–177° C.)

CALC: C, 69.63; H, 4.75; N, 16.92; FOUND: C, 69.58, 60,64; H, 5.00, 4.98; N, 16.66, 16.63

5-[3-Methoxy-4-(4-(2-quinolinylmethyloxy)benzyloxy)phenyl]tetrazole (M.P. 195°–97° C.)

CALC: C, 67.63; H, 4.88; N, 15.77; FOUND: C, 67.27; H, 4.89; N, 15.41.

5-[4-(3-(2-quinolinylmethyloxy)phenoxymethyl)-3-methoxyphenyl]-tetrazole (M.P. 189°–91° C.)

CALC: C, 66.95; H, 4.95; N, 15.61; FOUND: C, 66.48; H, 5.14; N, 14.93.

5-[3-(4-(2-quinolinylmethyloxy)phenoxymethyl)-phenoxymethyl)benzyl]tetrazole (M.P. 139°–44° C.)

CALC: C, 70.53; H, 5.03; N, 16.45; FOUND: C, 70.33, 70.54; H, 5.25, 5.36; N, 16.38, 16.41.

5-[4-(4-(2-quinolinylmethyloxy)phenoxymethyl)benzyl]tetrazole (M.P. 167°–71° C.)

CALC: C, 67.33; H, 5.31; N, 15.70; FOUND: C, 67.54, 67.67; H, 5.33, 5.33; N, 15.48, 15.52.

5-[4-Methoxy-3-(4-(2-quinolinylmethyloxy)phenylmethyloxy)phenyl]tetrazole (M.P. 210°–13° C.)

CALC: C, 68.33; H, 4.82; N, 4.90; FOUND: C, 68.32; H, 4.90; N, 14.79.

4-[3-(2-Quinolinylmethyloxy)phenoxymethyl]-phenoxyacetic acid (M.P. 164 (dec))

CALC: C, 69.27; H, 5,35; N, 3.23; FOUND: C, 69.53, 69.65; H, 5.11, 5.05; N, 3.21, 3.12.

5-[2-(4-(2-Quinolinylmethyloxy)phenoxymethyl)-phenoxymethyl]tetrazole (M.P. 183°–85° C.)

CALC: C, 65.63; H, 5.08; N, 15.31; FOUND C. 65.77, 65.52; H, 4.99, 5.03; N, 14.92, 15.03.

4-[4-(2-Quinolinylmethyloxy)phenoxymethyl)-phenoxyacetic acid (176° C. (dec))

CALC: C, 71.50; H, 5.16; N, 3.34; FOUND: C, 71.10, 71.17; H, 5.27, 5.33; N, 3.37, 3.34.

4-[3-(2-Quinolinylmethyloxy)phenoxymethyl]-phenylacetic acid (M.P. 158°–60° C.)

CALC: C, 75.17; H, 5.30; N, 3.51; FOUND: C, 74.89; H, 5.36; N, 3.37.

2-[3-(3-(2-Quinolinylmethyloxy)phenoxymethyl)-phenoxy]pentanoic acid (M.P. 133°–35° C.)

CALC: C, 73.51; H, 5.95; N, 3.06; FOUND: C, 73.35, 73.60; H, 5.95, 5.98; N, 3.08, 3.05.

2-[3-(2-Quinolinylmethyloxy)phenoxymethyl]-phenoxyacetic acid (M.P. 169°–172° C.)

CALC: C, 72.28; H, 5.10; N, 3.37; FOUND: C, 69.34, 69.69; H, 5.10, 5.13; N, 3.00, 3.08; CALC: C, 69.27; H, 5.35; N, 3.23 (as Hydrate).

2-[4-(2-Quinolinylmethyloxy)phenoxymethyl]cinnamic acid (M.P. 175°–178° C.)
CALC: C, 75.90; H, 5.14; N, 3.40; FOUND: C, 73.92; H, 5.20; N, 3.01; CALC: C, 74.27; H, 5.27; N, 3.33 (as Hydrate).

6-Acetyl-2-propyl-3-[3-(2-quinolinylmethyloxy)benzyloxy]phenoxyacetic acid (M.P. 153°–58° C.)
CALC: C, 72.13; H, 5.85; N, 2.90; FOUND: C, 71.68, 72.08; H, 5.88, 5.83; N, 2.65, 2.70.

2-[2-(4-(7-Chloroquinolin-2-ylmethyloxy)phenoxymethyl)phenoxy]propionic acid (M.P. 169°–173° C.)
CALC: C, 67.32; H, 4.78; N, 3.02; CI, 7.64; FOUND: C, 65.18; H, 4.90; N, 2.84; CI, 8.33; CALC: C, 65.41; H, 4.96; N, 2.93; CI, 7.42 (as HYDRATE).

2-[4-(2-Quinolinylmethyloxy)phenoxymethyl]phenylacetic acid (M.P. 181°–83° C.)
CALC: C, 75.17; H, 5.30; N, 3.51; FOUND: C, 75.12, 74.96; H, 5.50, 5.49; N, 3.16, 3.16.

3-[3-(2-Quinolinylmethyloxy)phenoxymethyl]phenoxyacetic acid (M.P. 146°–51° C.)
CALC: C, 72.28; H, 5.10; N, 3.37; FOUND: C, 71.82, 71.80; H, 5.24, 5.23; N, 2.98, 3.00; CALC: C, 71.50; H, 5.16; N, 3.34 (as HYDRATE).

2-[4-(2-Quinolinylmethyloxy)phenoxymethyl]phenoxyacetic acid (M.P. 153°–57° C.)
CALC: C, 72.28; H, 5.10; N, 3.37; FOUND: C, 72.30, 71.72; H, 5.39, 5.30; N, 2.94, 2.89.

5-[2-(4-(7-Chloroquinolin-2-ylmethyloxy)phenoxymethyl)benzyl]tetrazole (M.P. 159°–63° C.)
CALC: C, 65.57; H, 4.40; N, 15.29; FOUND: C, 64.16; H, 4.72; N, 14.98; CALC: C, 64.30; H, 4.53; N, 14.99 (as HYDRATE)

2-Carbomethoxy-5-[3-(2-quinolinylmethyloxy)phenoxymethyl]phenoxyacetic acid (M.P. 187°–89° C.)
CALC: C, 68.49; H, 4.90; N, 2.95; FOUND: C, 66.71; H, 4.96; N, 2.70; CALC: C, 66.59; H, 5.07; N, 2.87(as HYDRATE).

2-[3-(2-Quinolinylmethyloxy)phenoxymethyl]-6-methylphenoxyacetic acid (M.P. 149°–53° C.)
CALC: C, 72.71; H, 5.40; N, 3.26; FOUND: C, 71.23; H, 5.46; N, 3.08; CALC: C, 71.22; H, 5.51; N, 3.19 (as HYDRATE).

2-[3-(3-(2-Quinolinylmethyloxy)phenoxymethyl)phenoxy]glutaric acid (M.P. 129°–30° C.)
CALC: C, 69.00; H, 5.17; N, 2.87; FOUND: C, 58.19; H, 4.93; N, 2.23; CALC: C, 58.23; H, 5.17; N, 2.43 (as HYDRATE).

2-[3-(2-Quinolinylmethyloxy)phenoxymethyl]benzylmalonic acid (M.P. 164°–65° C.)
CALC: C, 70.89; H, 4.08; N, 3.06; FOUND: C, 70.51, 70.61; H, 5.03, 5.24; N, 3.03, 2.90.

2-[2-(3-Quinolinylmethyloxy)phenoxymethyl)phenoxy]pentanoic acid (M.P. 118°–20° C.)
CALC: C, 73.51; H, 5.95; N, 3.06; FOUND: C, 73.26; H, 6.07; N, 2.79.

2-[4-(2-Quinolinylmethyloxy)phenoxymethyl]-6-methylphenoxy acetic acid (M.P. 151°–53° C.)
CALC: C, 72.71; H, 5.40; N, 3.26; FOUND: C, 71.41; H, 5.58; N, 3.03; CALC: C, 71.22; H, 5.51; N, 3.19 (as HYDRATE).

2-[2-(4-(2-Quinolinylmethyloxy)phenoxymethyl)phenoxy]pentanoic acid (M.P. 85°–92° C.)
CALC: C, 73.51; H, 5.95; N, 3.06; FOUND: C, 71.73, 71.79; H, 5.96, 5.91; N, 3.06, 2.83; CALC: C, 72.09; H, 6.05; N, 3.00 (as HYDRATE).

2-Carbomethoxy-5-[4-(2-quinolinylmethyloxy)phenoxymethyl]phenoxyacetic acid (M.P. 149°–51° C.)
CALC: C, 68.49; H, 4.90; N, 2.95; FOUND: C, 68.00, 68.08; H, 4.98, 5.04; N, 2.90, 2.90.

2-[2-(4-(2-Quinolinylmethyloxy)phenoxymethyl)phenoxy]propionic acid (M.P. 161°–64° C.)
CALC: C, 72.71; H, 5.40; N, 3.26; FOUND: C, 70.96, 71.10; H, 5.51, 5.58; N, 3.08, 3.10; CALC: C, 71.22; H, 5.52; N, 3.19 (as HYDRATE).

2-[2-(3-(2-Quinolinylmethyloxy)phenoxymethyl)phenoxy]glutaric acid (M.P. 83° C.)
CALC: C, 68.98; H, 5.17; N, 2.87; FOUND: C, 64.10, 63.75; H, 4.89, 4.92; N, 2.64, 2.69; CALC: C, 63.74; H, 5.63; N, 2.65(as HYDRATE).

2-(3-[2-Quinolinylmethyloxy]benzyloxy)phenoxyacetic acid (M.P. 153°–55° C.)
CALC: C, 72.28; H, 5.10; N, 3.37; FOUND: C, 71.75; H, 5.14; N, 3.38; CALC: C, 71.50; H, 5.16; N, 3.34 (as HYDRATE).

2-[2-(4-(2-Quinolinylmethyloxy)phenoxymethyl]-4-chlorophenoxy)propionic acid (M.P. 196°–99° C.)
CALC: C, 67.32; H, 4.78; N, 3.02; FOUND: C, 67.40, 67.43; H, 4.89, 4.94; N, 3.01, 3.13.

2-[2-(3-(2-Quinolinylmethyloxy)phenoxymethyl]-4-chlorophenoxy)propionic acid (M.P. 169°–71° C.)
CALC: C, 67.32; H, 4,78; N, 3.02; FOUND: C, 65.47; H, 5.31; N, 2.78; CALC: C, 65.41; H, 4.96; N, 2.93(as HYDRATE).

2-(2-[3-(2-Quinolinylmethyloxy)phenoxymethyl]-4-chlorophenoxy)pentanoic acid (M.P. 144°–4520 C.)
CALC: C, 68.36; H, 5,33; N, 2.85; FOUND: C, 67.74, 67.86; H, 5.39, 5.47; N, 2.91, 2.84; CALC: C, 67.74; H, 5.38; N, 2.82(as HYDRATE).

2-(2-[4-(2-Quinolinylmethyloxy)phenoxymethyl]-4-chlorophenoxy)pentanoic acid (M.P. 155°–56° C.)
CALC: C, 68.36; H, 5.33; N, 2.85; FOUND: C, 65.96; H, 5.59; N, 2.66; CALC: C, 65.95; H, 5.53; N, 2.75(as HYDRATE).

2-(2-[4-(2-Quinolinylmethyloxy)phenoxymethyl]-4-chlorophenoxy)pentanoic acid (M.P. 155°–56° C.)
CALC: C, 68.36; H, 5.33; N, 2.85; FOUND: C, 66.15; H, 5.58; N, 2.68; CALC: C, 65.95; H, 5.53; N, 2.75(as HYDRATE).

2-(2-[4-(2-Quinolinylmethyloxy)phenoxymethyl]-6-chlorophenoxy)pentanoic acid (M.P. 161°–62° C.)
CALC: C, 68.36; H, 5.33; N, 2.85; FOUND: C, 68.15; H, 5.36; N, 2.72.

2-(2-[3-(2-Quinolinylmethyloxy)phenoxymethyl]-6-chlorophenoxy)pentanoic acid (M.P. 169°–70° C.)
CALC: C, 68.36; H, 5.33; N, 2.85; FOUND: C, 68.10; H, 5.39; N, 2.72.

2-(2-[3-(2-Quinolinylmethyloxy)phenoxymethyl]-6-chlorophenoxy)-4-methylpentanoic acid (M.P. 164°–66° C.)
CALC: C, 68.84; H, 5.58; N, 2.77; FOUND: C, 68.84; H, 5.70; N, 2.69.

2-(2-[4-(2-Quinolinylmethyloxy)phenoxymethyl]-6-chlorophenoxy)-4-methylpentanoic acid (M.P. 167°–69° C.)
CALC: C, 68.84; H, 5.58; N, 2.77; FOUND: C, 68.78; H, 5.67; N, 2.68.

5-[3-(3-(2-Quinolinylmethyloxy)benzyloxy)-4-methoxyphenyl]tetrazole (M.P. 204°–07° C.)
CALC: C, 67.63; H, 4.88; N, 15.78; FOUND: C, 67.11; H, 5.15; N, 15.86

N-[3-Methoxy-4-(3-(2-quinolinylmethyloxy)benzyloxy)benzoyl benzene sulphonamide hydrochloride (M.P. dec.88)

CALC: C, 62.99; H, 4.60; N, 4,74; FOUND: C, 63,88; H, 5.13; N, 4.80;

5-Carboxy-2-(3-(2-quinolinylmethyloxy)phenoxymethyl)phenoxy acetic acid (M.P. 226°-28° C.)
CALC: C, 61.90; H, 5.18; N, 2.77; FOUND: C, 61.62; H, 5.11; N, 2.67.

5-[3-Methoxy-4-(3-(2-quinolinylmethyloxy)benzyloxy)phenyl]tetrazole (M.P. 204°-05° C.)
CALC: C, 67.67; H, 5.14; N, 15.87; FOUND: C, 67.63; H, 4.88; N, 15.78.

5-4-(3-(2-quinolinylmethyloxy)benzyloxy)phenyl)tetrazole (M.P. 233°-36° C.)
CALC: C, 69.58; H, 4.73; N, 16.91; FOUND: C, 69.59; H, 4.89; N, 16.91.

Using a combination of the above Examples, various compounds may be made within the scope of this invention.

We claim:
1. A compound of the formula

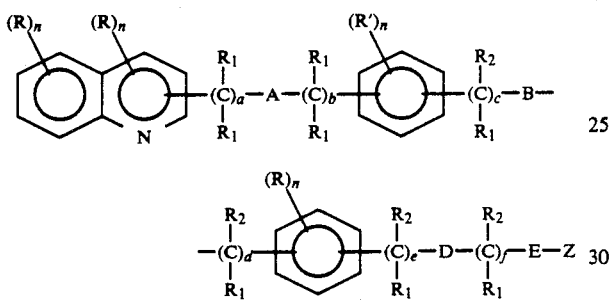

where:
A is O or S;
B is O, S, SO, SO2NR1,

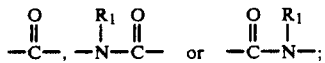

D is O, S, NR,

or a chemical bond;
E is a chemical bond or

a is 0-2;
b is 0-1;
c is 0-4;
d is 0-5;
e is 0-4;
f is 0-5;
n is 0-2;
R is independently hydrogen, alkyl, hydroxy, alkoxy, carboxy, carbalkoxy, halo, nitro, haloalkyl, cyano or acyl;
R' is independently hydrogen, alkyl, hydroxy, alkoxy, halo or haloalkyl;
R1 is independently hydrogen, alkyl or aralkyl;
R2 is —(CH2)$_x$—X, where x is 0-3;
X is hydrogen, alkyl, alkenyl, cycloalkyl, aryl aralkyl, hydroxy, alkoxy, aralkoxy, amino, mono-and dialkylamino, aralkylamino, acylamino, carbamyl, carboxy, carbalkoxy, tetrazolyl, or acylsulfonamido;
vicinal R2 groups together may be (CH2)$_y$— where y is 1-4, thus forming a 3-6 membered ring;
geminal R1 and R2 groups may together form a spiro substituent, —(CH2)$_z$—; were z is 2 to 5;
geminal R1 or R1 and R2 groups may together form an alkylidenyl substituent, =CHR1;
Z is —COOR1, CN,

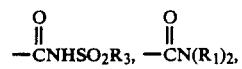

—OR1, tetrazolyl or substituted tetrazolyl where the substituent may be alkyl, carboxyalkyl or carbalkoxyalkyl; and
R3 is hydrogen, alkyl, haloalkyl, phenyl or benzyl; or a pharmaceutically acceptable salt thereof.

2. A compound according to claim 1 where:
A is O or S;
B is O or S;
n is 0-1;
a+b is 1;
c+d is 1-2;
e+f is 0-5;
R and R' are hydrogen, alkyl or alkoxy;
R1 is hydrogen or alkyl;
R2 is —(CH2)$_x$—X where x is 0-3 and X is hydrogen or alkyl; and
Z is —COOR1, —CN,

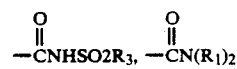

or tetrazolyl.

3. A compound according to claim 2 where:
A and B are O;
n is 0;
c+d is 1; and
Z is —COOR1, —CN or tetrazolyl.

4. A compound according to claim 3 where:
a is 1; b is 0; c is 1; and d is 0.

5. A compound according to claim 4 where: D is O; and E is a chemical bond.

6. A compound according to claim 4 where:
D is S; and E is a chemical bond.

7. A compound according to claim 4 where:
e+f is 0; D is a chemical bond; and
E is a chemical bond.

8. A compound according to claim 4 where:
e+f is 1-5; D is a chemical bond; and
E is a chemical bond.

9. A compound according to claim 4 where:
D is O; and
E is

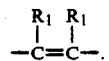

10. A compound according to claim 4 where:
D is a chemical bond or and
E is

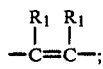

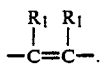

11. A compound according to claim 3 where:
a is 1; b is 0; c is 0; and d is 1.

12. A compound according to claim 2 where:
is 1; b is 0; c is 0; and d is 2.

13. A compound according to claim 11 where:
D is O; and E is a chemical bond.

14. A compound according to claim 11 where:
c+f is 0; D is a chemical bond; and E is a chemical bond.

15. A compound according to claim 13 where e+f is 1-5.

16. A compound according to claim 7 which is 5-(3-(3-(2-quinolinylmethyloxy)benzyloxy)phenyl)tetrazole or a pharmaceutically acceptable salt thereof.

17. A compound according to claim 7 which is 5-[4-(3-(2-quinolinylmethyloxy)phenoxymethyl)phenoxymethyl)phenyl]tetrazole or a pharmaceutically acceptable salt thereof.

18. A compound according to claim 7 which is 5-[3-methoxy-4-(3-(2-quinolinylmethyloxy)benzyloxy)-phenyl]tetrazole or a pharmaceutically acceptable salt thereof.

19. A compound according to claim 7 which is 5-[4-methoxy-3-(3-(2-quinolinylmethyloxy)benzyloxy)-phenyl]tetrazole or a pharmaceutically acceptable salt thereof.

20. A compound according to claim 7 which is 5-[4-(4-(2-quinolinylmethyloxy)benzyloxy)phenyl]tetrazole or a pharmaceutically acceptable salt thereof.

21. A compound according to claim 8 which is 5-[4-(4-(2-quinolinylmethyloxy)benzyloxy)benzyl]tetrazole or a pharmaceutically acceptable salt thereof.

22. A compound according to claim 8 which is 5-[4-(3-(4-(2-quinolinylmethyloxy)benzyloxy)phenyl)-3-methylbutyl]tetrazole or a pharmaceutically acceptable salt thereof.

23. A compound according to claim 14 which is 5-[3-(3-(2-quinolinylmethyloxy)phenoxymethyl)phenyl]tetrazole or a pharmaceutically acceptable salt thereof.

24. A compound according to claim 14 which is 5-[2-(3-(2-quinolinylmethyloxy)phenoxymethyl)phenyl]tetrazole or a pharmaceutically acceptable salt thereof.

25. A compound according to claim 14 which is 5-[4-(3-(2-quinolinylmethyloxy)phenoxymethyl))phenyl]tetrazole or a pharmaceutically acceptable salt thereof.

26. A compound according to claim 14 which is 4-(3-(2-quinolinylmethyloxy)phenoxymethyl)benzonitrile or a pharmaceutically acceptable salt thereof.

27. A compound according to claim 14 which is 4-(3-(2-quinolinylmethyloxy)phenoxymethyl)benzoic acid or a pharmaceutically acceptable salt thereof.

28. A compound according to claim 14 which is 3-(3-(2-quinolinylmethyloxy)phenoxymethyl)benzoic acid or a pharmaceutically acceptable salt thereof.

29. A compound according to claim 15 which is α-(3-(4-(2-quinolinylmethyloxy)phenoxymethyl)phenoxy)acetonitrile or a pharmaceutically acceptable salt thereof.

30. A compound according to claim 15 which is 5-[4-(3-(2-quinolinylmethyloxy)phenoxymethyl)phenoxymethyl]tetrazole or a pharmaceutically acceptable salt thereof.

31. A compound according to claim 15 which is 5-[4-(3-(2-quinolinylmethyloxy)phenoxymethyl)phenoxymethyl]tetrazole or a pharmaceutically acceptable salt thereof.

32. A compound according to claim 15 which is 5-[3-(3-(2-quinolinylmethyloxy)phenoxymethyl)phenoxymethyl]tetrazole or a pharmaceutically acceptable salt thereof.

33. A compound according to claim 15 which is 5-carboxy-2-(3-(2-quinolinylmethyloxy)phenoxymethyl)-phenoxyacetic acid or a pharmaceutically acceptable salt thereof.

34. A compound according to claim 15 which is 5-[2-(3-(2-quinolinylmethyloxy)phenoxymethyl)phenoxymethyl]tetrazole or a pharmaceutically acceptable salt thereof.

35. A compound according to claim 15 which is 5-[2-(3-(2-quinolinylmethyloxy)phenoxymethyl)5-carbomethoxyphenoxymethyl]tetrazole or a pharmaceutically acceptable salt thereof.

36. A compound according to claim 7 which is 3-methoxy-4-(3-(2-quinolinylmethyloxy)benzyloxy)benzoic acid or a pharmaceutically acceptable salt thereof.

37. A compound according to claim 7 which is methyl 3-methoxy-4-(3-(2-quinolinylmethyloxy)benzyloxy)benzoate or a pharmaceutically acceptable salt thereof.

38. A compound according to claim 2 which is 5-[3-methoxy-4-(3-(2-quinolinylmethyloxy)phenyoxymethyl)phenyl]tetrazole or a pharmaceutically acceptable salt thereof.

39. A compound according to claim 2 which is N-[3-methoxy-4-(3-(2-quinolinylmethyloxy)benzyloxy)benzoyl] benzenesulfonamide or a pharmaceutically acceptable salt thereof.

40. A compound according to claim 14 which is 3-methoxy-4-(3-(2-quinolinylmethyloxy)phenoxymethyl)benzoic acid or a pharmaceutically acceptable salt thereof.

41. A compound according to claim 1 which is 5-[2-(4-(2-quinolinylmethyloxy)phenoxymethyl)benzyl]tetrazole or a pharmaceutically acceptable salt thereof.

42. A method for the treatment of hypersensitive ailments in humans and mammals comprising administering thereto an effective amount of a compound of the formula according to claim 1.

43. A pharmaceutical composition wherein the active ingredient is a compound according to claim 1 in admixture with a pharmaceutical carrier.

* * * * *

UNITED STATES PATENT AND TRADEMARK OFFICE
CERTIFICATE OF CORRECTION

PATENT NO. : 5,059,610

DATED : October 22, 1991

INVENTOR(S) : *Fu-chi Huang et al.*

It is certified that error appears in the above-identified patent and that said Letters Patent is hereby corrected as shown below:

At column 1, line 39, please insert --,-- between the words "$SO_2$" and "$NR_1$".

At column 2, line 19, please insert --,-- between the words "aryl" and "aralkyl";
line 21, please delete "mono-and" and insert -- mono- and -- therefor;
line 29, please delete the "CH" and insert "CN" therefor.

At column 3, line 66, please delete $-\overset{\overset{O}{\|}}{C}NHSO2R_3$ and insert -- $-\overset{\overset{O}{\|}}{C}NHSO_2R_3$ -- therefor.

At column 6, line 8, please delete "or SO" and insert --or $SO_2$-- therefor;
line 55, please delete "These" and insert --Those-- therefor.

At column 10, line 36, please delete " the this" and insert --the-- therefor.

At column 12, line 63, please delete "administer-ed" and insert --administered-- therefore.

At column 14, line 26, please delete "CHCl3" and insert "$CHCl_3$" therefor;
line 29, please delete "NaHCO3" and insert "$NaHCO_3$" therefor;
line 56, please delete "cl";
line 56, "TABLE III" should be on the following new line.

UNITED STATES PATENT AND TRADEMARK OFFICE
CERTIFICATE OF CORRECTION

PATENT NO. : 5,059,610

DATED : October 22, 1991

INVENTOR(S) : *Fu-chi Huang et al.*

It is certified that error appears in the above-indentified patent and that said Letters Patent is hereby corrected as shown below:

At column 16, line 7, please delete "of" and insert --then the-- therefor;

lines 35-36, please delete "5-[2-(3-(4(2-quinolinylmethyloxy)benzyloxy)phenyl)propyl]tetrazole" and insert --5-[2-(3-(4-(2-quinolinylmethyloxy)benzyloxy)phenyl)propyl]tetrazole-- therefor;

lines 37-38, please delete "5-[2-(3-(4(2-quinolinylmethyloxy)benzyloxy)phenyl)butyl]tetrazole" and insert --5-[2-(3-(4-(2-quinolinylmethyloxy)benzyloxy)phenyl)butyl]tetrazole-- therefor;

lines 39-40, please delete "5-[3-(3-(4(2-quinolinylmethyloxy)benzyloxy)phenyl)butyl]tetrazole" and insert --5-[3-(3-(4-(2-quinolinylmethyloxy)benzyloxy)phenyl)butyl]tetrazole-- therefor.

At column 17, line 27, and at column 19, line 18, please delete "H2O" and insert --$H_2O$-- therefore;

line 29, please delete "HO" and insert --$H_2O$-- therefore.

At column 20, line 18, please delete "5-methyoxy-3(2-quinolinylmethyloxy)phenol" and insert --5-methoxy-3(2-quinolinylmethyloxy)phenol-- therefor.

At column 25, line 12, please delete "α(3-hydroxymethylphenoxy)acetonitrile" and insert --α-(3-hydroxymethylphenoxy)acetonitrile-- therefor;

line 13-14, please delete "α(4-hydroxymethylphenoxy)acetonitrile" and insert --α-(4-hydroxymethylphenoxy)acetonitrile-- therefor;

line 19, please delete "α(3-hydroxymethylphenoxy)acetonitrile" and insert --α-(3-hydroxymethylphenoxy)acetonitrile-- therefor;

UNITED STATES PATENT AND TRADEMARK OFFICE
CERTIFICATE OF CORRECTION

PATENT NO. : 5,059,610
DATED : October 22, 1991
INVENTOR(S) : Fu-chi Huang et al.

It is certified that error appears in the above-identified patent and that said Letters Patent is hereby corrected as shown below:

line 20-21, please delete "α(2-hydroxymethylphenoxy)acetonitrile" and insert --α-(2-hydroxymethylphenoxy)acetonitrile-- therefor;

line 21-22, please delete "α[(2-hydroxymethyl-5-carbomethoxy)phenoxy)acetonitrile" and insert --α-[(2-hydroxymethyl-5-carbomethoxy)phenoxy)acetonitrile -- therefor;

line 46 and 48, please delete "Table XIII" and insert --Table XIIIa-- therefor.

At column 26, line 18, please delete "3-(4'-hydroxybutyl)phenol" and insert --3-(4'-hydroxybutyl)phenyl-- therefor;

line 19, please delete "4-(4'-hydroxybutyl)phenol" and insert --4-(4'-hydroxybutyl)phenyl-- therefor;

line 28 and 29, please delete "Table XIII" and insert --Table XIIIb-- therefor.

At column 27, lines 1-2, please delete "5-(3-(3-(2-quinolinylmethyloxy)-4-methoxyphenoxymethyl)phenoxymethyl)tetrazole" and insert --5-(3-(3-(2-quinolinylmethyloxy)-4-methylphenoxymethyl)phenoxymethyl)tetrazole -- therefor.

At column 29, lines 25-26, please delete "5-(4-(3-(2-Quinolinylmethyloxy)Phenoxymethyl)-Phenyl)Tetrazol-3-Yl) Acetic Acid" and insert --5-(4-(3-(2-Quinolinylmethyloxy)Phenoxymethyl)-Phenyl)Tetrazol-3-yl) Acetic Acid-- therefor.

UNITED STATES PATENT AND TRADEMARK OFFICE
CERTIFICATE OF CORRECTION

PATENT NO. : 5,059,610
DATED : October 22, 1991
INVENTOR(S) : Fu-chi Huang et al.

It is certified that error appears in the above-identified patent and that said Letters Patent is hereby corrected as shown below:

At column 33, line 3, please delete "spiro-(3,3-cyclopropane)4-chlorobutyronitrile" and insert -- spiro-(3,3-cyclopropane)-4-chlorobutyronitrile-- therefor.

At column 36, lines 34-35, please delete "5-[3-(4-(2-quinolinylmethyloxy)phenoxymethyl)-phenoxymethyl)benzyl]tetrazole" and insert --5-[3-(4-(2-quinolinylmethyloxy)phenoxymethyl)benzyl]tetrazole-- therefor.

At column 39, line 35, please delete "SO2NR$_1$" and insert --SO$_2$, NR$_1$-- therefor;
line 66, please delete "-(CH2)$_X$ -X" and insert -- -(CH$_2$)$_X$ -X- -- therefor;
line 68, please delete " mono-and" and insert -- mono- and -- therefor.

At column 40, line 37, please delete $-\overset{\overset{O}{\|}}{C}NHSO2R_3$ and insert -- $-\overset{\overset{O}{\|}}{C}NHSO_2R_3$ -- therefor.

At column 41, lines 29-30, please delete "5-[4-(3-(2-quinolinylmethyloxy)phenoxymethyl)phenoxymethyl)phenyl]tetrazole" and insert --5-[4-(3-(2-quinolinylmethyloxy)phenoxymethyl)phenyl]tetrazole-- therefor.

UNITED STATES PATENT AND TRADEMARK OFFICE
CERTIFICATE OF CORRECTION

PATENT NO. : 5,059,610

DATED : October 22, 1991

INVENTOR(S) : *Fu-chi Huang et al.*

It is certified that error appears in the above-identified patent and that said Letters Patent is hereby corrected as shown below:

At column 42, lines 11-12, please delete "5-[4-(3-(2-quinolinylmethyloxy)phenoxymethyl)phenoxymethyl]tetrazole" and insert --5-[3-(4-(2-quinolinylmethyloxy)phenoxymethyl)phenoxymethyl]tetrazole-- therefor.

Signed and Sealed this

Twenty-first Day of July, 1998

Attest:

*Attesting Officer*

BRUCE LEHMAN

*Commissioner of Patents and Trademarks*